US009259542B2

(12) United States Patent
Acker et al.

(10) Patent No.: US 9,259,542 B2
(45) Date of Patent: Feb. 16, 2016

(54) RESPIRATORY MONITORING WITH DIFFERENTIAL PRESSURE TRANSDUCER

(75) Inventors: Jaron Matthew Acker, Madison, WI (US); Robert Quin Yew Tham, Middleton, WI (US); Kristopher John Bilek, Madison, WI (US); Andreas Tzanetakis, Helsinki (FI)

(73) Assignee: General Electric Company, Schenectady, NY (US)

( * ) Notice: Subject to any disclaimer, the term of this patent is extended or adjusted under 35 U.S.C. 154(b) by 1973 days.

(21) Appl. No.: 11/613,988

(22) Filed: Dec. 20, 2006

(65) Prior Publication Data

US 2007/0125380 A1    Jun. 7, 2007

Related U.S. Application Data

(63) Continuation-in-part of application No. 11/285,121, filed on Nov. 22, 2005, now Pat. No. 7,422,015.

(51) Int. Cl.
*A61B 5/08* (2006.01)
*A61B 5/087* (2006.01)
*A61B 5/091* (2006.01)
*A61M 16/06* (2006.01)
*A61M 16/00* (2006.01)

(52) U.S. Cl.
CPC .............. *A61M 16/00* (2013.01); *A61B 5/087* (2013.01); *A61B 5/08* (2013.01); *A61B 5/0816* (2013.01); *A61B 5/0826* (2013.01); *A61B 5/091* (2013.01); *A61M 16/06* (2013.01); *A61M 16/0627* (2014.02); *A61M 2016/0036* (2013.01); *A61M 2230/40* (2013.01)

(58) Field of Classification Search
CPC .............. A61M 16/00; A61M 16/06; A61M 2016/0036; A61M 2230/40; A61B 5/08; A61B 5/0816; A61B 5/0826; A61B 5/087; A61B 5/091
USPC .......................................... 600/529–543, 484
See application file for complete search history.

(56) References Cited

U.S. PATENT DOCUMENTS 3,742,939 A * 7/1973 Sayer ............................ 600/533
4,054,133 A   10/1977 Myers
4,258,710 A   3/1981 Reber
(Continued)

FOREIGN PATENT DOCUMENTS

DE    3708146 A1    9/1988
EP    1800707       6/2007
(Continued)

OTHER PUBLICATIONS

Chinese Office Action dated Dec. 16, 2010 (translated).
(Continued)

*Primary Examiner* — Navin Natnithithadha
(74) *Attorney, Agent, or Firm* — Andrus Intellectual Property Law, LLP

(57) ABSTRACT

A differential pressure transducer determines pressure differentials between respiratory airflows and ambient airflows. Another determines pressure differentials between respiratory airflows and interface airflows. And another determines pressure differentials between i) respiratory airflows received from a subject and ii) interface airflows received from an area near a cannula. Corresponding respiratory monitoring methods also determine the same.

20 Claims, 19 Drawing Sheets

(56) References Cited

U.S. PATENT DOCUMENTS

| | | | |
|---|---|---|---|
| 5,137,017 A | 8/1992 | Salter | |
| 5,400,781 A | 3/1995 | Davenport | |
| 5,474,060 A | 12/1995 | Evans | |
| 5,704,345 A * | 1/1998 | Berthon-Jones | 128/204.23 |
| 5,868,133 A * | 2/1999 | DeVries et al. | 128/204.21 |
| 6,017,315 A * | 1/2000 | Starr et al. | 600/538 |
| 6,029,665 A * | 2/2000 | Berthon-Jones | 128/204.23 |
| 6,138,675 A * | 10/2000 | Berthon-Jones | 128/204.23 |
| 6,152,129 A | 11/2000 | Berthon-Jones | |
| 6,155,986 A | 12/2000 | Brydon et al. | |
| 6,253,764 B1 | 7/2001 | Calluaud | |
| 6,279,569 B1 | 8/2001 | Berthon-Jones | |
| 6,342,040 B1 * | 1/2002 | Starr et al. | 600/538 |
| 6,363,933 B1 * | 4/2002 | Berthon-Jones | 128/204.23 |
| 6,367,474 B1 * | 4/2002 | Berthon-Jones et al. | 128/204.23 |
| 6,422,240 B1 | 7/2002 | Levitsky et al. | |
| 6,425,395 B1 * | 7/2002 | Brewer et al. | 128/202.22 |
| 6,439,234 B1 | 8/2002 | Curti et al. | |
| 6,484,719 B1 * | 11/2002 | Berthon-Jones | 128/204.23 |
| 6,502,572 B1 * | 1/2003 | Berthon-Jones et al. | 128/204.23 |
| 6,526,970 B2 * | 3/2003 | DeVries et al. | 128/204.21 |
| 6,532,957 B2 * | 3/2003 | Berthon-Jones | 128/204.21 |
| 6,544,192 B2 * | 4/2003 | Starr et al. | 600/538 |
| 6,575,163 B1 * | 6/2003 | Berthon-Jones | 128/204.18 |
| 6,588,422 B1 | 7/2003 | Berthon-Jones et al. | |
| 6,644,311 B1 * | 11/2003 | Truitt et al. | 128/204.22 |
| 6,655,385 B1 | 12/2003 | Curti et al. | |
| 6,659,101 B2 | 12/2003 | Berthon-Jones | |
| 6,668,828 B1 * | 12/2003 | Figley et al. | 128/204.18 |
| 6,675,797 B1 * | 1/2004 | Berthon-Jones | 128/204.23 |
| 6,688,307 B2 * | 2/2004 | Berthon-Jones | 128/204.23 |
| 6,810,876 B2 * | 11/2004 | Berthon-Jones | 128/204.21 |
| 6,814,073 B2 * | 11/2004 | Wickham | 128/204.18 |
| 6,817,361 B2 * | 11/2004 | Berthon-Jones et al. | 128/204.18 |
| 6,849,049 B2 * | 2/2005 | Starr et al. | 600/538 |
| 6,945,248 B2 | 9/2005 | Berthon-Jones | |
| 6,986,351 B2 * | 1/2006 | Figley et al. | 128/205.24 |
| 6,988,498 B2 * | 1/2006 | Berthon-Jones et al. | 128/204.23 |
| 7,007,694 B2 | 3/2006 | Aylsworth et al. | |
| 7,013,893 B2 * | 3/2006 | Wickham et al. | 128/204.23 |
| 7,055,522 B2 | 6/2006 | Berthon-Jones | |
| 7,137,389 B2 * | 11/2006 | Berthon-Jones | 128/204.18 |
| 7,159,588 B2 * | 1/2007 | Wickham | 128/204.23 |
| 7,305,988 B2 * | 12/2007 | Acker et al. | 128/204.18 |
| 7,320,320 B2 * | 1/2008 | Berthon-Jones | 128/204.23 |
| 7,422,015 B2 * | 9/2008 | Delisle et al. | 128/207.18 |
| 7,644,713 B2 * | 1/2010 | Berthon-Jones | 128/204.21 |
| 7,730,886 B2 * | 6/2010 | Berthon-Jones | 128/204.23 |
| 7,762,253 B2 * | 7/2010 | Acker et al. | 128/204.26 |
| 7,845,350 B1 * | 12/2010 | Kayyali et al. | 128/204.23 |
| 2002/0017300 A1 | 2/2002 | Hickle et al. | |
| 2002/0029004 A1 | 3/2002 | Starr et al. | |
| 2002/0043264 A1 * | 4/2002 | Wickham | 128/204.18 |
| 2002/0116994 A1 | 8/2002 | Heinonen | |
| 2003/0130591 A1 * | 7/2003 | Starr et al. | 600/538 |
| 2004/0074492 A1 * | 4/2004 | Berthon-Jones | 128/200.24 |
| 2004/0163647 A1 * | 8/2004 | Figley et al. | 128/204.18 |
| 2005/0005942 A1 | 1/2005 | Aylsworth et al. | |
| 2005/0011523 A1 | 1/2005 | Aylsworth et al. | |
| 2005/0039750 A1 * | 2/2005 | Wickham et al. | 128/204.23 |
| 2005/0121033 A1 | 6/2005 | Starr et al. | |
| 2005/0217668 A1 * | 10/2005 | Figley et al. | 128/200.23 |
| 2006/0005835 A1 * | 1/2006 | Berthon-Jones | 128/204.23 |
| 2007/0113847 A1 * | 5/2007 | Acker et al. | 128/204.18 |
| 2007/0113848 A1 * | 5/2007 | Acker et al. | 128/204.18 |
| 2007/0113850 A1 * | 5/2007 | Acker et al. | 128/204.22 |
| 2007/0113851 A1 * | 5/2007 | Delisle et al. | 128/204.23 |
| 2007/0113856 A1 * | 5/2007 | Acker et al. | 128/207.14 |
| 2007/0125380 A1 * | 6/2007 | Acker et al. | 128/204.23 |
| 2007/0144518 A1 * | 6/2007 | Acker et al. | 128/204.21 |
| 2008/0078393 A1 * | 4/2008 | Acker et al. | 128/204.29 |

FOREIGN PATENT DOCUMENTS

| | | |
|---|---|---|
| WO | 01/95971 A | 12/2001 |
| WO | WO2005067520 | 7/2005 |
| WO | WO2007033347 | 3/2007 |

OTHER PUBLICATIONS

Unofficial translation of Search Report from SIPO for CN Application No. 200610172866.6 dated Jun. 23, 2013.

Search Report and Written Opinion from EP Application No. 07110198.4 dated Jan. 22, 2009.

Search Report and Written Opinion from EP Application No. 06124280.6 dated Jan. 14, 2009.

* cited by examiner

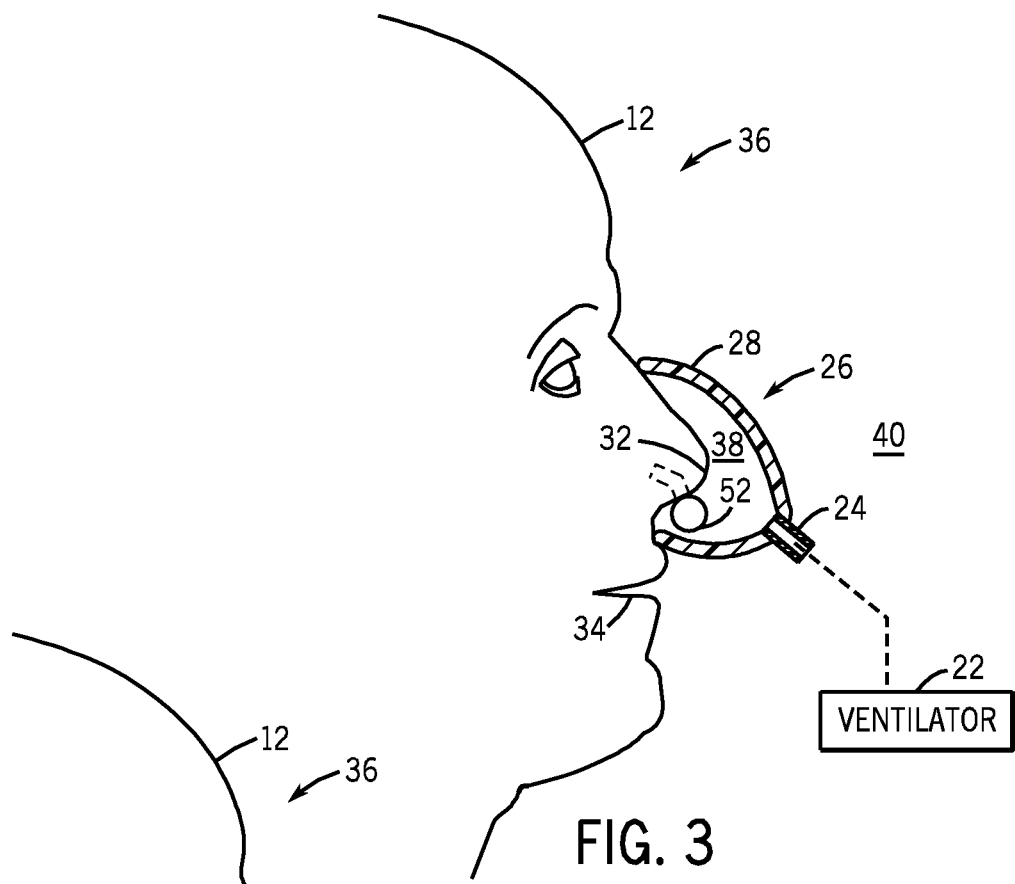
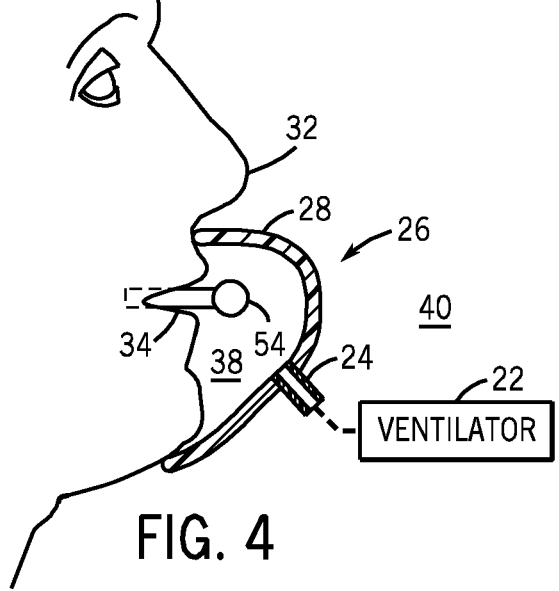
FIG. 3
FIG. 4

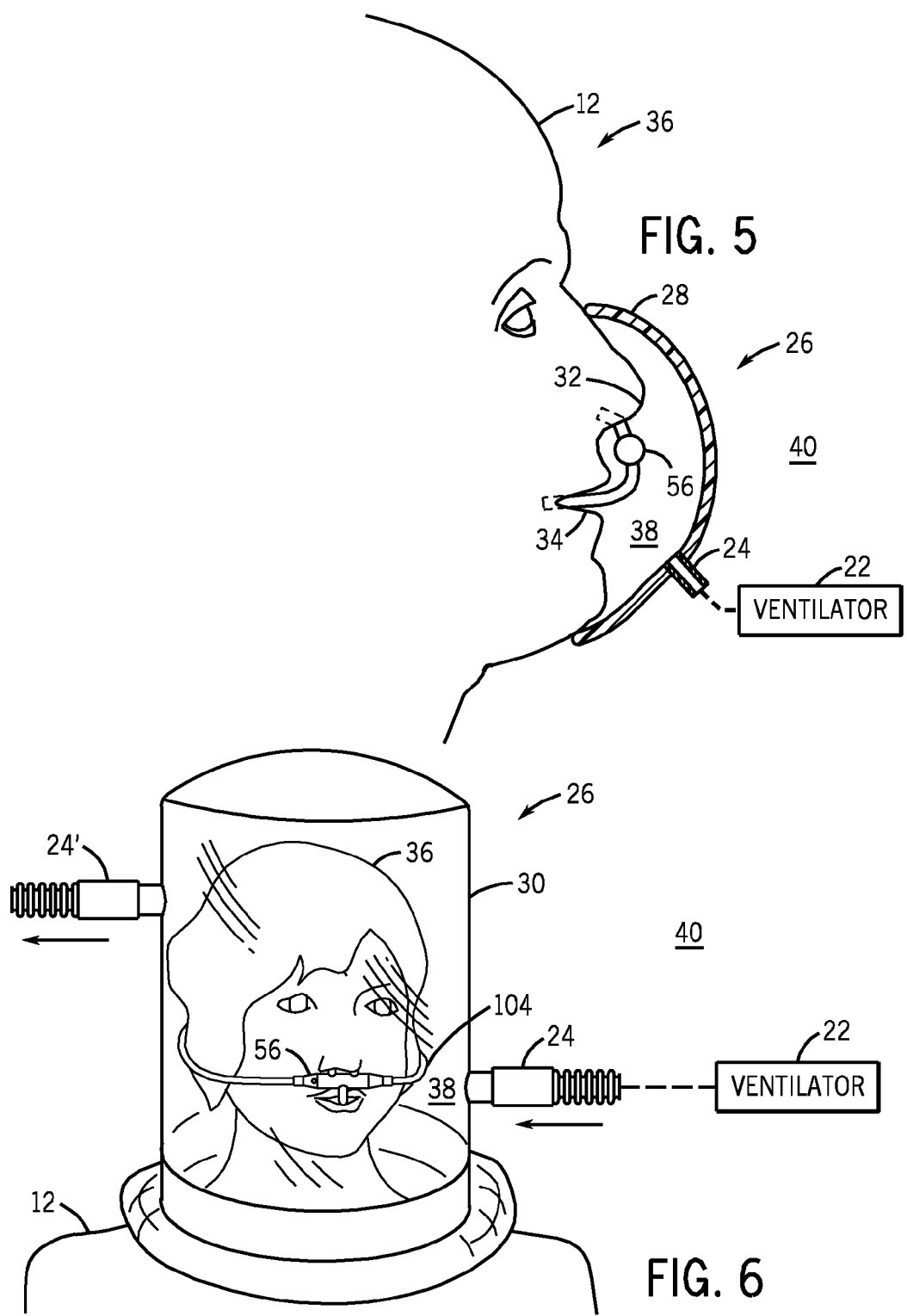

| RESPIRATORY AIRFLOW | INTERFACE AIRFLOW | RESULTING PRESSURE DIFFERENTIAL? | LIKELY SIGNIFICANCE |
|---|---|---|---|
| INCREASE | INCREASE | NO | NON-RESPIRATORY EVENT / LIKELY COMPRESSION |
| INCREASE | NO CHANGE OR DECREASE | YES | RESPIRATORY EVENT / EXHALE |
| DECREASE | DECREASE | NO | NON-RESPIRATORY EVENT / LIKELY LEAK |
| DECREASE | NO CHANGE OR INCREASE | YES | RESPIRATORY EVENT / INHALE |

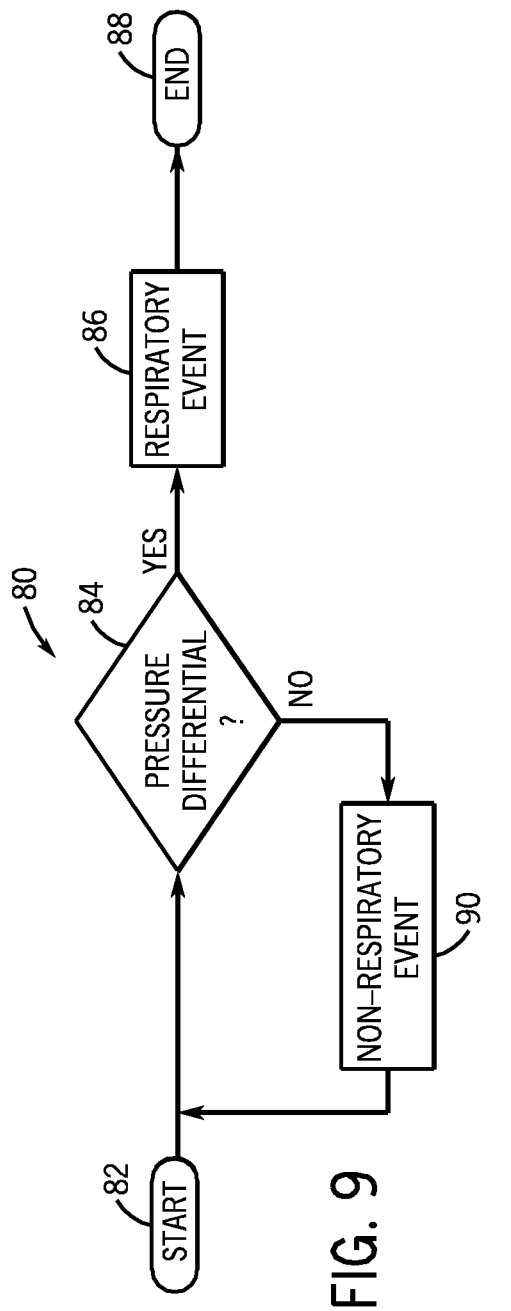

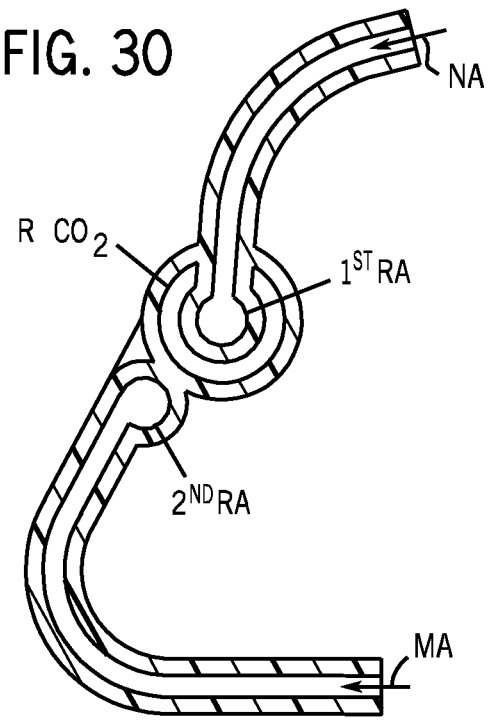
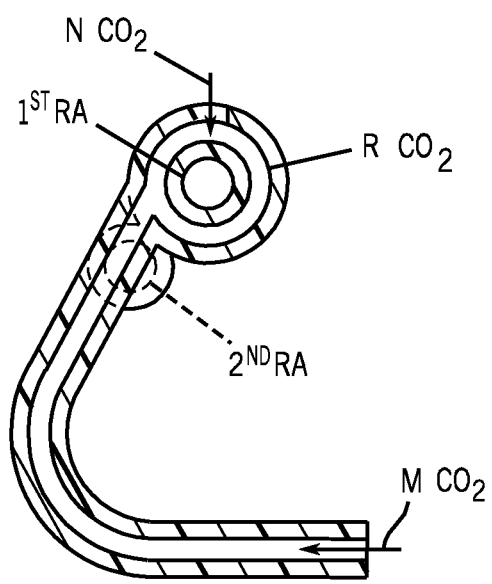

FIG. 35

| | SINGLE PRONG | MULTIPLE PRONGS | PARTITION | ORIFICE(S) | DIRECT CONNECTION THROUGH CANNULA | OPEN CONNECTION WITH INTERFACE | SINGLE RESPIRATORY AIRFLOW | MULTIPLE RESPIRATORY AIRFLOWS | SINGLE DIFFERENTIAL PRESS. X-DUCER | MULTIPLE DIFFERENTIAL PRESS. X-DUCERS | PURGE | CALIBRATION VALUES | $P_{gage}$ | EXHALED GAS SAMPLING | BIFURCATED PRONG(S) | OFFSET PRONG(S) | SCOOPED PRONG(S) | CAPTURE ENHANCER | VENTILATOR CONTROL |
|---|---|---|---|---|---|---|---|---|---|---|---|---|---|---|---|---|---|---|---|
| ORO CANNULA | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ |
| NASAL CANNULA | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ |
| ORO-NASAL CANNULA | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ |

RESPIRATORY MONITORING WITH DIFFERENTIAL PRESSURE TRANSDUCER

CROSS-REFERENCE(S) TO RELATED APPLICATION(S)

This application is a continuation-in-part of U.S. patent application Ser. No. 11/315,751, which was filed on Dec. 22, 2005 and entitled "Integrated Ventilator Nasal Trigger and Gas Monitoring System" and Ser. No. 11/285,121, which was filed on Nov. 22, 2005 and entitled "Arrangement and Method for Detecting Spontaneous Respiratory Effort of a Patient."

STATEMENT REGARDING FEDERALLY SPONSORED RESEARCH OR DEVELOPMENT

-

REFERENCE(S) TO MICROFICHE APPENDIX AND/OR COPYRIGHT PROTECTION

-

BACKGROUND

1. Field

In general, the inventive arrangements relate to respiratory care, and more specifically, to improvements in respiratory monitoring.

2. Description of Related Art

For illustrative, exemplary, representative, and non-limiting purposes, preferred embodiments of the inventive arrangements will be described in terms of medical subjects needing respiratory care. However, the inventive arrangements are not limited in this regard.

Now then, referring generally, when a subject is medically unable to sustain breathing activities on the subject's own, mechanical ventilators can improve the subject's condition and/or sustain the subject's life by assisting and/or providing requisite pulmonary gas exchanges on behalf of the subject. Not surprisingly, many types of mechanical ventilators are well-known, and they can be generally classified into one (1) of three (3) broad categories: spontaneous, assisted, and/or controlled mechanical ventilators.

During spontaneous ventilation, a subject generally breathes at the subject's own pace, but various, external factors can affect certain parameters of the ventilation, such as tidal volumes and/or baseline pressures within a system. With this first type of mechanical ventilation, the subject's lungs still "work," in varying degrees, and the subject generally tends and/or tries to use the subject's own respiratory muscles and/or reflexes to control as much of the subject's own breathing as the subject can.

During assisted or self-triggered ventilation, the subject generally initiates breathing by inhaling and/or lowering a baseline pressure, again by varying degrees, after which a clinician and/or ventilator then "assists" the subject by applying generally positive pressure to complete the subject's next breath.

During controlled or mandatory ventilation, the subject is generally unable to initiate breathing by inhaling and/or exhaling and/or otherwise breathing naturally, by which the subject then depends on the clinician and/or ventilator for every breath until the subject can be successfully weaned therefrom.

Now then, as is well-known, non-invasive mechanical ventilation can be improved upon by containing and/or controlling the spaces surrounding the subject's airways in order to achieve more precise control of the subject's gas exchanges. Commonly, this is accomplished by applying i) an enclosed facemask, which can be sealably worn over the subject's nose, mouth, and/or both, or ii) an enclosed hood or helmet, which can be sealably worn over the subject's head, the goals of which are to at least partly or wholly contain and/or control part or all of the subject's airways. Referring generally, these types of arrangements are known as "interfaces," a term that will be used hereinout to encompass all matters and forms of devices that can be used to secure subject airways in these fashions.

During non-invasive mechanical ventilation, it is increasingly important to monitor the subject's respiration and/or other respiratory airflows, at least to access the adequacy of ventilation and/or control operation of attached ventilators. For example, interface leaks and/or interface compressions commonly adversely effect a subject's interpreted and/or real airflow needs. More specifically, since interface disturbances will always be difficult and/or impossible to avoid, a need exists to deal with them appropriately.

In accordance with all or part of the foregoing, the inventive arrangements address interface disturbances and respiratory airflows, particularly during non-invasive spontaneous and/or assisted mechanical ventilation.

SUMMARY

In one embodiment, a differential pressure transducer determines pressure differentials between respiratory airflows and ambient airflows.

In another embodiment, a differential pressure transducer determines pressure differentials between respiratory airflows and interface airflows.

In yet another embodiment, a differential pressure transducer determines pressure differentials between i) respiratory airflows received from a subject and ii) interface airflows received from an area near a cannula.

In yet still another embodiment, a respiratory monitoring method determines pressure differentials between respiratory airflows and ambient airflows.

In a further embodiment, a respiratory monitoring method determines pressure differentials between respiratory airflows and interface airflows.

In an additional embodiment, a respiratory monitoring method determines pressure differentials between i) respiratory airflows received from a subject and ii) interface airflows received from an area near a cannula.

BRIEF DESCRIPTION OF SEVERAL VIEWS OF THE DRAWINGS

A clear conception of the advantages and features constituting inventive arrangements, and of various construction and operational aspects of typical mechanisms provided by such arrangements, are readily apparent by referring to the following illustrative, exemplary, representative, and non-limiting figures, which form an integral part of this specification, in which like numerals generally designate the same elements in the several views, and in which:

FIG. 2 illustrates a well-known Bernoulli effect, whereby pressures vary in accordance with airflows generated in a pitot tube or the like.

FIG. 3 is a sectional side-view of a subject using a nasal cannula within an interface.

FIG. 4 is a sectional side-view of a subject using an oral cannula within an interface.

FIG. 5 is a sectional side-view of a subject using an oro-nasal cannula within an interface.

FIG. 6 is a front view of a subject using the oro-nasal cannula of FIG. 5 within another interface.

FIG. 9 is a flow chart determining pressure differentials to distinguish respiratory and/or non-respiratory events.

FIG. 10 is an event table determining pressure differentials to distinguish likely respiratory and/or non-respiratory events.

FIG. 30 is a second cut-away view taken along line 30-30 in FIG. 28.

FIG. 31 is a third cut-away view taken along line 31-31 in FIG. 28.

FIG. 35 is a table depicting various combinations of some or all of the variously described attributes.

DETAILED DESCRIPTION OF PREFERRED EMBODIMENTS

Referring now to the figures, preferred embodiments of the inventive arrangements will be described in terms of medical subjects needing respiratory care. However, the inventive arrangements are not limited in this regard. For example, while variously described embodiments provide improvements in respiratory care, and more specifically, improvements in respiratory monitoring, such as cannular improvements, particularly suited for use during non-invasive spontaneous and/or assisted mechanical ventilation, other contexts are also hereby contemplated, including various other healthcare, consumer, industrial, radiological, and inspection systems, and the like.

Figure 1:
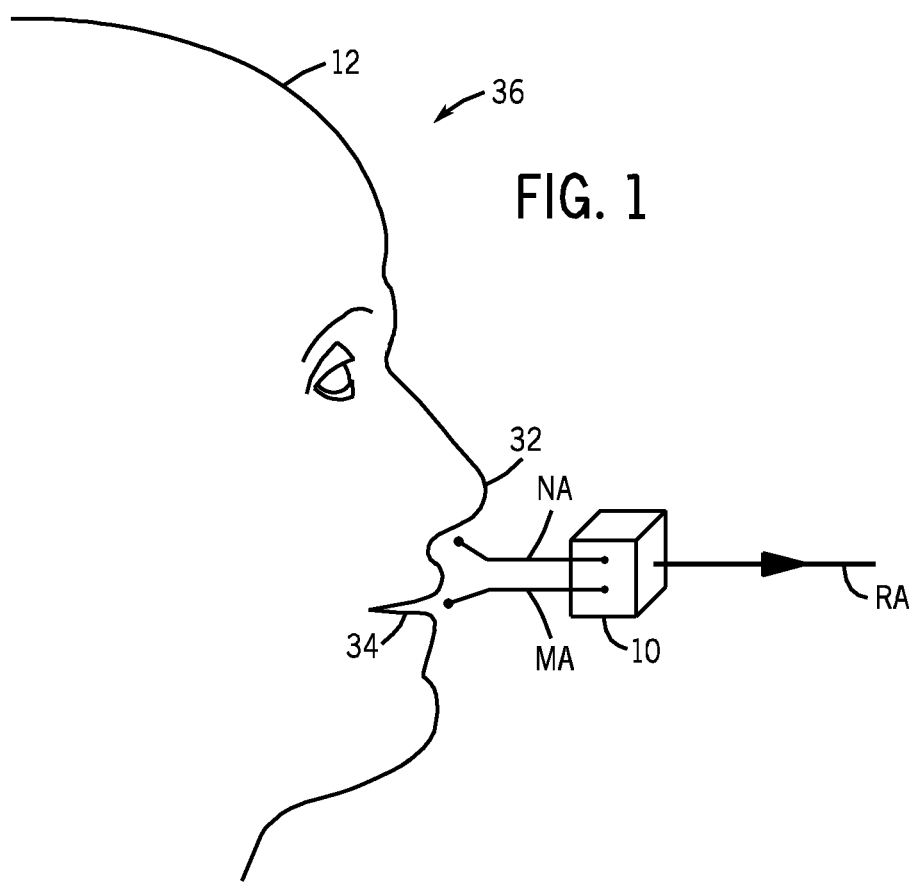
FIG. 1 depicts generic monitoring of a subject's respiratory airflows.

Referring now to FIG. 1, a sensor 10 is configured to receive at least partial and/or full sampling of a subject's 12 nasal airflows ("NA") and mouth airflows ("MA") as respiratory airflows ("RA"). Preferably, the sensor 10 is in communication with downstream electrical and/or pneumatic circuitry (not shown in FIG. 1) that measures the strength of the respiratory airflows RA and outputs a signal indicative thereof. Accordingly, changes in the nasal airflows NA and mouth airflows MA past the sensor 10 can be detected. More particularly, the term "airflow," in these contexts, will be used hereinout to encompass generalized disturbances (e.g., compression and/or decompressions) of a column of air held in dynamic suspension between the sensor 10 and subject 12.

Figure 2:
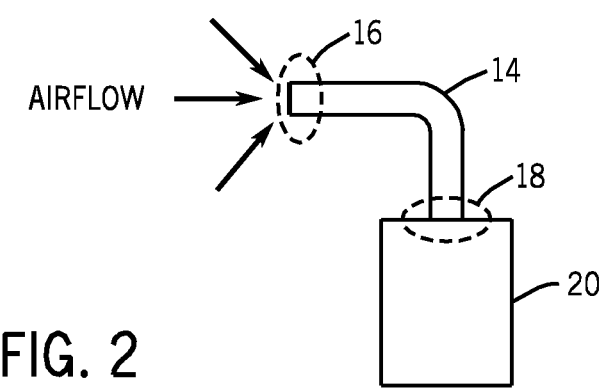

Referring now to FIG. 2, pressures, which vary with airflow rates, are generated in a tube 14, such as a pitot tube, by placing an open end 16 thereof in parallel with, or at some intermediate angle to, various airflows. Another, more distal end 18 of the tube 14 terminates at a pressure measuring and/or sensing device 20, such as an electrical pressure transducer, the output of which varies in accordance with the airflows.

Now then, referring more specifically, the pitot tube is a well-known hollow tube that can be placed, at least partially, longitudinally to the direction of airflows, allowing the same to enter an open end thereof at a particular approach velocity. After the airflows enter the pitot tube, they eventually come to a stop at a so-called stagnation point, at which point their velocity energy is transformed into pressure energy, the latter of which can be detected by the electrical pressure transducer. Bemouli's equation can be used to calculate the static pressure at the stagnation point. Then, since the velocities of the airflows within the pitot tube are zero at the stagnation point, downstream pressures can be calculated.

Referring now to FIGS. 3-6, the subject 12 receives ventilator support from a ventilator 22 via a breathing conduit 24. More specifically, the breathing conduit 24 communicates with the subject 12 between the ventilator 22 and an interface 26, which, for example, in the embodiment shown in FIGS. 3-5, is a generally enclosed mask or facemask 28, and, in the embodiment shown in FIG. 6, is a generally enclosed hood or helmet 30, the interfaces 26 of which are suitable for maintaining positive airway ventilation pressure within the interface 26. More specifically, for example, the mask or facemask 28 can be sealably worn over a nose 32 and/or mouth 34 of the subject 12, while the hood or helmet 30 can be sealably worn over a head 36 of the subject 12, the sealing of which is designed to at least partly or wholly contain and/or control part or all of the subject's 12 airways. Accordingly, a sealed area 38 within each interface 26 is created, the area 38 being reasonably sealed from an area 40 external the interface 26. In other words, interface airflows IA within the area 38 of each interface 26 are generally independent of airflows in the area 40 external from the interface 26, and/or vice-versa.

Now then, as shown in FIG. 1, it is also possible to eliminate the interface 26, in which case the interface airflows IA become ambient airflows AA, particularly as the area 38 within the interface 26 and the area 40 external the interface 26 merge to become indistinct and/or non-separable. In this context, the interface airflows IA and ambient airflows AA are one in the same.

Otherwise, each interface 26 is adapted to provide a closed connection between one or more of the subject's 12 breathing passages, such as the subject's 12 nasal passages and/or oral passages, and the ventilator 22. Accordingly, the ventilator 22 and interface 26 are suitably arranged to provide a flow of breathing gases to and/or from the subject 12 through the breathing conduit 24. This arrangement is generally known as the breathing circuit.

In FIGS. 3-6, the subject 12 wears a cannula 50, such as a nasal cannula 52 (e.g., see FIG. 3), oral cannula 54 (e.g., see FIG. 4), and/or oro-nasal cannula 56 (e.g., see FIGS. 5-6). More specifically, each of the depicted cannulas 50 is configured to communicate with and/or receive respiratory airflows RA from the subject 12 and interface airflows IA from the area 38 within the interface 26 and/or ambient airflows AA.

Now then, a goal of respiratory care is to detect changes in the subject's 12 respiratory airflows RA, thereby triggering an appropriate response by the ventilator 22. However, disturbances to the interface 26 can hinder this objective. For example, if a leak or compression develops at and/or about the interface 26, the ventilator 22 could mistakenly interpret a respiratory event as a non-respiratory event, and/or vice-versa. For example, if pressure drops within the area 38 of the interface 26, the ventilator 22 could interpret this pressure drop as indicating the subject's 12 attempt to initiate inhalation, thus responding accordingly. However, if the pressure drop within the area 38 of the interface 26 was instead triggered by an interface leak somewhere between the subject 12 and the ventilator 22 in the breathing circuit, then the ventilator 22 could likely mis-interpret the pressure drop and/or mis-respond in properly ventilating the subject 12. Similarly, if pressure increases within the area 38 of the interface 26, the ventilator 22 could interpret this pressure increase as indicating the subject's 12 attempt to initiate exhalation, thus responding accordingly. However, if the pressure increase within the area 38 of the interface 26 was instead triggered by interface compression somewhere between the subject 12 and the ventilator 22 in the breathing circuit, then the ventilator 22 could likely mis-interpret the pressure increase and/or mis-respond in properly ventilating the subject 12. Accordingly, attempts to decrease false reads within the area 38 of the interface 26 are always desired.

Referring now more generally, one of the major issues with non-invasive mechanical ventilation are the occurrences of these leaks and/or compressions in the interface 26 and/or breathing circuit. These disturbances result in the ventilator's 22 inability to accurately assess the respiratory needs and/or efforts of the subject 12. However, accurately assessing the respiratory needs and/or efforts of the subject 12 is necessary to accurately synchronize the assistance of the mechanical ventilation.

Typically, these respiratory needs and/or efforts of the subject 12 have been detected by placing a pressure sensor within the ventilator 22 and/or interface 26. However, when leaks and/or compressions in the interface 26 occur with conventional pressure sensors, the ventilator 22 only sees a resulting flow or pressure change about the area 38 within the interface 26, and it interprets it as the subject's attempt to breath in or out. Accordingly, the ventilator 22 will not provide the proper ventilator support to the subject 12, particularly if the leaks and/or compressions remain undetected and/or undetectable.

Now then, recognition is made of the fact that differences in the respiratory airflows RA and interface flows IA and/or ambient airflows AA can be used to decrease these false reads. More specifically, if precise and accurate determinations can be made between the respiratory airflows RA and interface airflows IA and/or ambient airflows AA, then falsely interpreting what is happening at the area 38 within the interface 26 can be minimized and/or altogether eliminate. For example, if the interface 26 and/or breathing circuit develops a leak, then both the respiratory airflows RA and interface airflows IA will be similarly effected—i.e., they will both trend in parallel and both decrease, in which case the ventilator 22 can suspend interpreting the pressure decrease as the subject's 12 attempt to inhale. Similarly, if the interface 26 and/or breathing circuit is compressed, then both the respiratory airflows RA and interface airflows IA will be similarly effected—i.e., they will both trend in parallel and both increase, in which case the ventilator 22 can suspend interpreting the pressure increase as the subject's 12 attempt to exhale. Accordingly, whenever there is a disturbance (e.g., a leak and/or compression) in the interface 26 and/or breathing circuit, pressure at all sensing ports will change by an equal amount, such that all of the relative differential pressures therebetween will remain unchanged. Therefore, only changes in respiratory airflows RA for which there is not a corresponding change in interface airflows IA will be interpreted as a respiratory event, and vice-versa.

Figures 7, 8:
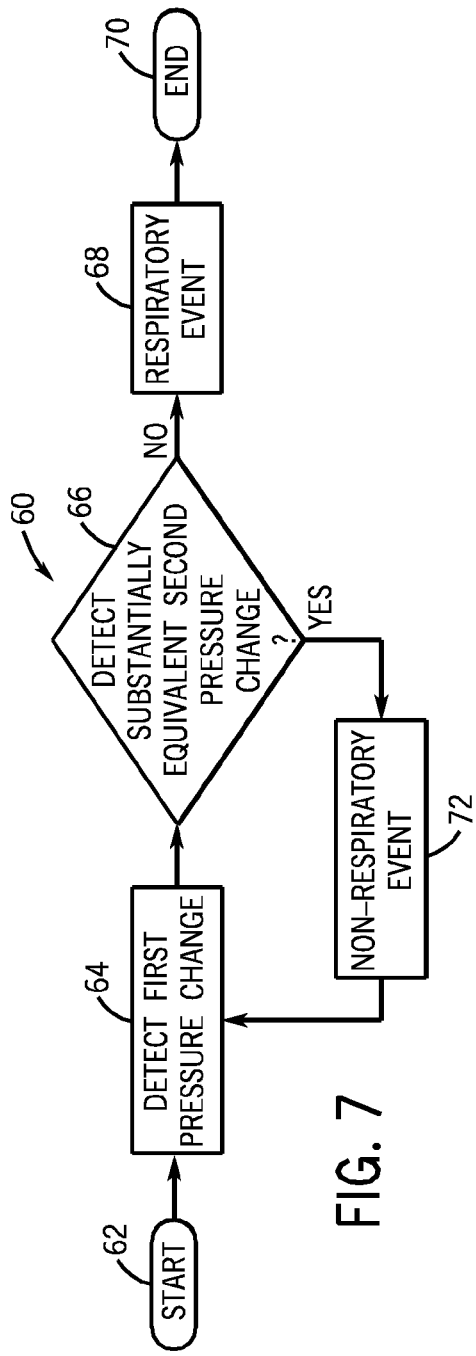
FIG. 7 is a flow chart comparing first and second pressure changes to distinguish respiratory and/or non-respiratory events.
FIG. 8 is an event table comparing respiratory airflows and interface airflows to determine resulting pressure differentials to distinguish the likely significance of various respiratory and/or non-respiratory events.

Referring now to FIG. 7, the afore-described principles of operation will be summarized in terms of a flowchart 60. More specifically, a methodology begins at a step 62, after which a first pressure change is detected in a step 64. At a subsequent step 66, it is determined whether a substantially equivalent second pressure change was detected. If a substantially equivalent second pressure change was not detected in step 66, then it is concluded that there was a respiratory event, as indicated in step 68, after which the method then terminates in a step 70 and the ventilator 22 responds appropriately through the breathing conduit 24 and/or breathing circuit. Alternatively, however, if a substantially equivalent second pressure change was detected in step 66, then it is concluded that there was not a respiratory event, as indicated in step 72, after which control iteratively returns to step 64 to detect another first pressure change. In this fashion, corresponding differential pressure changes are sensed between the respiratory airflows RA and interface airflows IA and/or ambient airflows AA for properly interpreting the same, particularly as respiratory or non-respiratory events.

Referring now to FIG. 8, interface leaks and/or interface compressions commonly adversely effect the subject's 12 interpreted and/or real airflow needs, as previously mentioned. Now then, if the subject's 12 respiratory airflows RA increase at the same time and/or in the same way that the interface airflows IA increase, then a pressure differential between the two will not develop, signifying a non-respiratory event, such as a likely compression of the interface 26. In other words, the increase in respiratory airflow RA, while ordinarily signifying a subject's attempt to breath out, is properly understood in this context to instead likely mean that the interface 26 was compressed, as per the corresponding increase in the interface airflows IA.

However, if the subject's 12 respiratory airflows RA increase at the same time that the interface airflows IA decrease or stay the same, then a pressure differential between the two will develop, signifying a respiratory event, such as the subject's 12 likely attempt to exhale. In other words, the increase in respiratory airflow RA, while ordinarily signifying the subject's 12 attempt to breath out, is properly understood in this context to mean that the subject 12 did indeed likely attempt to exhale, as per the corresponding no change or decrease in the interface airflows IA.

Similarly, if the subject's 12 respiratory airflows RA decrease at the same time and/or in the same way that the interface airflows IA decrease, then a pressure differential between the two will not develop, again signifying a non-respiratory event, such as a likely leak at the interface 26. In other words, the decrease in respiratory airflow RA, while ordinarily signifying the subject's 12 attempt to breath in, is properly understood in this context to instead likely mean that the interface 26 developed a leak, as per the corresponding decrease in the interface airflows IA.

However, if the subject's 12 respiratory airflows RA decrease at the same time that the interface airflows IA increase or stay the same, then a pressure differential between the two will develop, signifying a respiratory event, such as the subject's 12 likely attempt to inhale. In other words, the decrease in respiratory airflow RA, while ordinarily signifying a subject's 12 attempt to breath in, is properly understood in this context to mean that the subject 12 did indeed likely attempt to inhale, as per the corresponding no change or increase in the interface airflows IA.

These above-described scenarios are presented in an event table 74 in FIG. 8.

Referring now to FIG. 9, the afore-described principals of operation will be summarized in terms of another flowchart 80. More specifically, a methodology begins at a step 82, after which it is determined whether a pressure differential was detected in a step 84. If a pressure differential was detected in step 84, then it is concluded that there was a respiratory event, as indicated in step 86, after which the method then terminates in a step 88 and the ventilator 22 responds appropriately through the breathing conduit 24 and/or breathing circuit. Alternatively, if a pressure differential was not detected in step 84, then it is concluded that there was not a respiratory event, as indicated in step 90, after which control iteratively returns to step 84 to detect another pressure differential. In this fashion, corresponding differential pressure changes are sensed between the respiratory airflows RA and interface airflows IA and/or ambient airflows AA for properly interpreting the same, particularly as respiratory or non-respiratory events.

Referring now to FIG. 10, resulting pressure differentials between the respiratory airflows RA and interface airflows IA generally signify respiratory events, while a lack thereof generally signifies non-respiratory events.

These above-described scenarios are presented in an event table 92 in FIG. 10.

Figure 11:
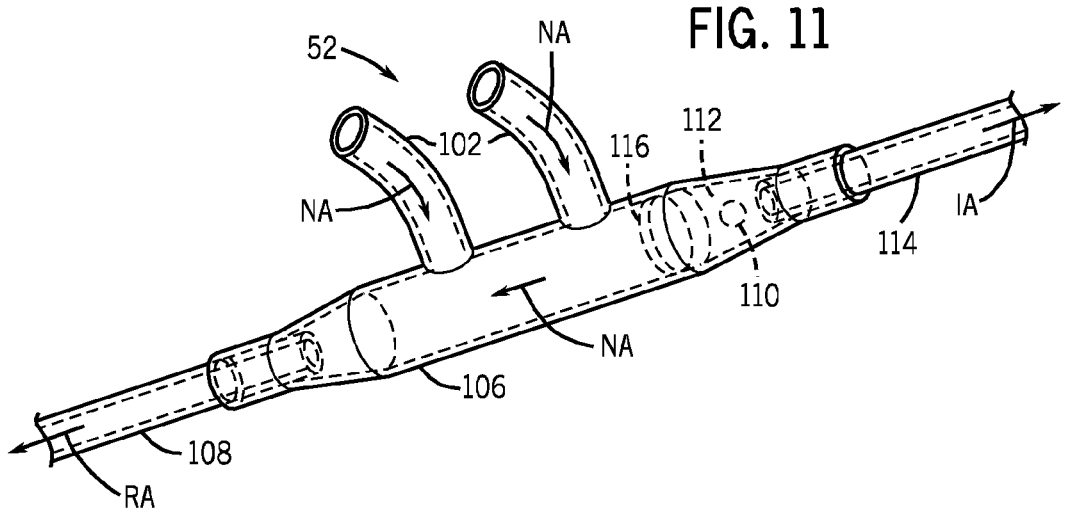
FIG. 11 is a front-perspective view of a nasal cannula receiving the following:
  i) nasal airflows as respiratory airflows; and
  ii) interface airflows.
Figure 12:
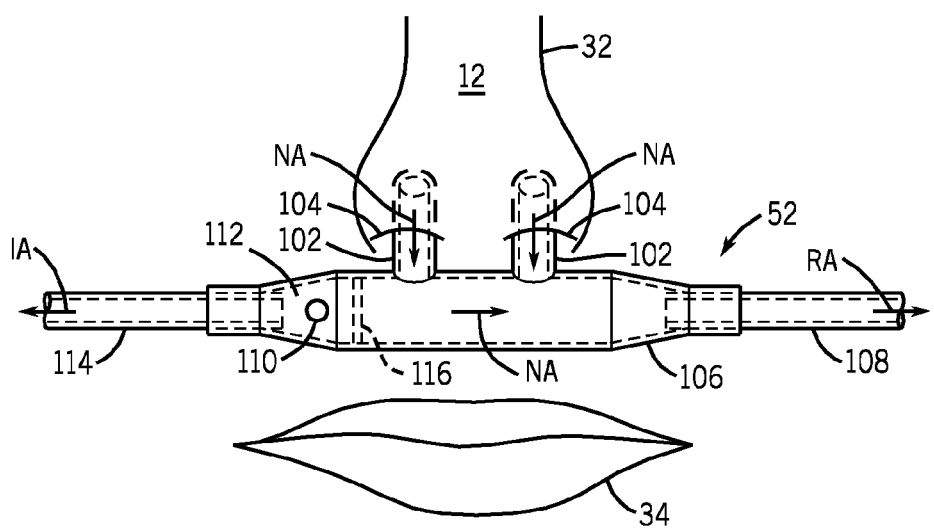
FIG. 12 is a front view of the nasal cannula of FIG. 11.

Referring now to FIGS. 11-12, a nasal cannula 52 is adapted to receive i) nasal airflows NA, and ii) interface airflows IA. More specifically, the nasal cannula 52 includes one or more nasal prongs 102 that are adapted to fit within one or more nares 104 of the nose 32 of the subject 12, particularly for communicating with and/or receiving and/or carrying the nasal airflows NA therefrom. The nasal airflows NA are then communicated by and/or received by and/or carried by a body 106 of the cannula 50 from the nasal prongs 102 to a respiratory lumen 108. More specifically, the nasal cannula 52 is adapted to receive the nasal airflows NA as respiratory airflows RA for communication to a pneumatic circuit (not shown in FIGS. 11-12) via the respiratory lumen 108. Preferably, the nasal prongs 102 are of suitable size and shape for insertion into the lower portions of the subject's 12 nares 104 without unduly blocking the nasal airflows NA into the area 38 within the interface 26.

In addition, the body 106 of the cannula 50 preferably contains an interface orifice 110 on an external surface 112 thereof, particularly for communicating with and/or receiving and/or carrying the interface airflows IA therefrom, as received by and/or in the area 38 within the interface 26. The interface airflows IA are then communicated by and/or received by and/or carried by the body 106 of the cannula 50 from the interface orifice 110 to an interface lumen 114. More specifically, the cannula 50 is adapted to receive the interface airflows IA for communication to the pneumatic circuit via the interface lumen 114.

Preferably, the respiratory airflows RA and interface airflows IA are received on opposing sides of a dividing partition 116 internally disposed within the body 106 of the cannula 50. Preferably, this partition 116 is configured to divide the body 106 of the cannula 50 into one or more chambers, at least one of which is configured to receive the respiratory airflows RA and at least one of which is configured to receive the interface airflows IA.

Figure 13:
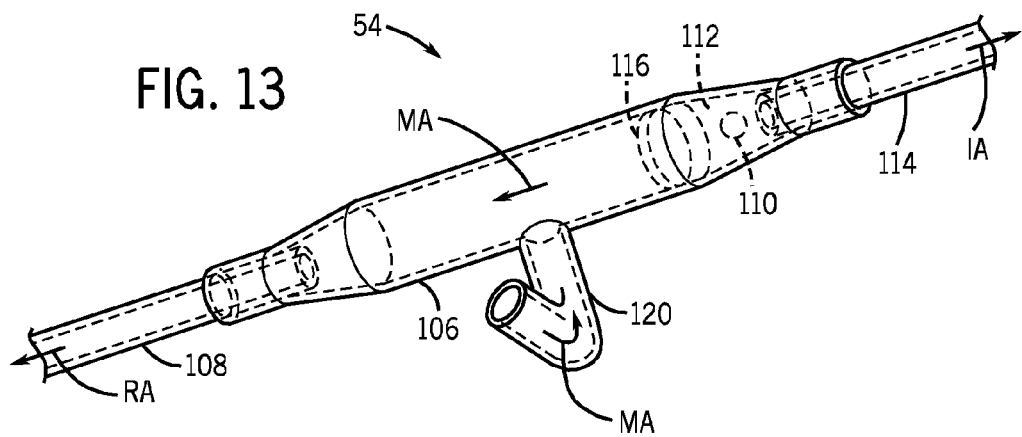
FIG. 13 is a front-perspective view of an oral cannula receiving the following:
  i) mouth airflows as respiratory airflows; and
  ii) interface airflows.
Figure 14:
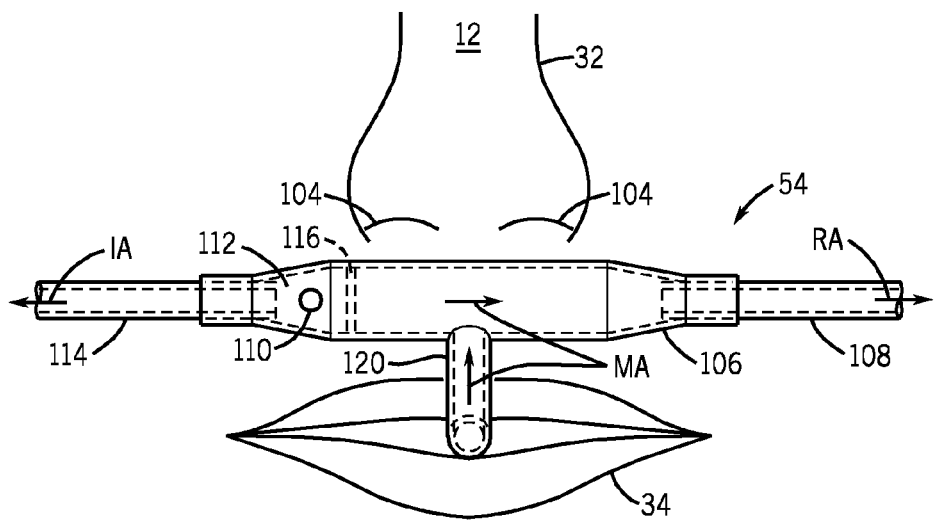
FIG. 14 is a front view of the oral cannula of FIG. 13.

Referring now to FIGS. 13-14, an oral cannula 54 is adapted to receive i) mouth airflows MA, and ii) interface airflows IA. More specifically, the oral cannula 54 includes one or more mouth prongs 120 that are adapted to fit within the mouth 34 of the subject 12, particularly for communicating with and/or receiving and/or carrying the mouth airflows MA therefrom. The mouth airflows MA are then communicated by and/or received by and/or carried by the body 106 of the cannula 50 from the mouth prongs 120 to the respiratory lumen 108. More specifically, the oral cannula 54 is adapted to receive the mouth airflows MA as respiratory airflows RA for communication to a pneumatic circuit (not shown in FIGS. 13-14) via the respiratory lumen 108. Preferably, the mouth prongs 120 are of suitable size and shape for insertion into the subject's 12 mouth 34 without unduly blocking the mouth airflows MA into the area 38 within the interface 26. Preferably, the horizontal location of the mouth prongs 120 may be the saggital midline of the subject's 12 mouth 34. If needed and/or desired, however, it can also be offset from the midline, for example, if there are multiple mouth prongs 120 (only one of which is shown in the figure). In either case, the mouth prongs 120 should be located approximately in the center of the mouth airflows MA in and/or out of the subject's 12 slightly opened mouth 34.

In addition, the body 106 of the cannula 50 preferably contains the interface orifice 110 on the external surface 112 thereof, particularly for communicating with and/or receiving and/or carrying the interface airflows IA therefrom, as received by and/or in the area 38 within the interface 26. The interface airflows IA are then communicated by and/or received by and/or carried by the body 106 of the cannula 50 from the interface orifice 110 to the interface lumen 114. More specifically, the cannula 50 is adapted to receive the interface airflows IA for communication to the pneumatic circuit via the interface lumen 114.

Preferably, the respiratory airflows RA and interface airflows IA are received on opposing sides of the dividing partition 116 internally disposed within the body 106 of the cannula 50. Preferably, this partition 116 is configured to divide the body 106 of the cannula 50 into the one or more chambers, at least one of which is configured to receive the respiratory airflows RA and at least one of which is configured to receive the interface airflows IA.

Figure 15:
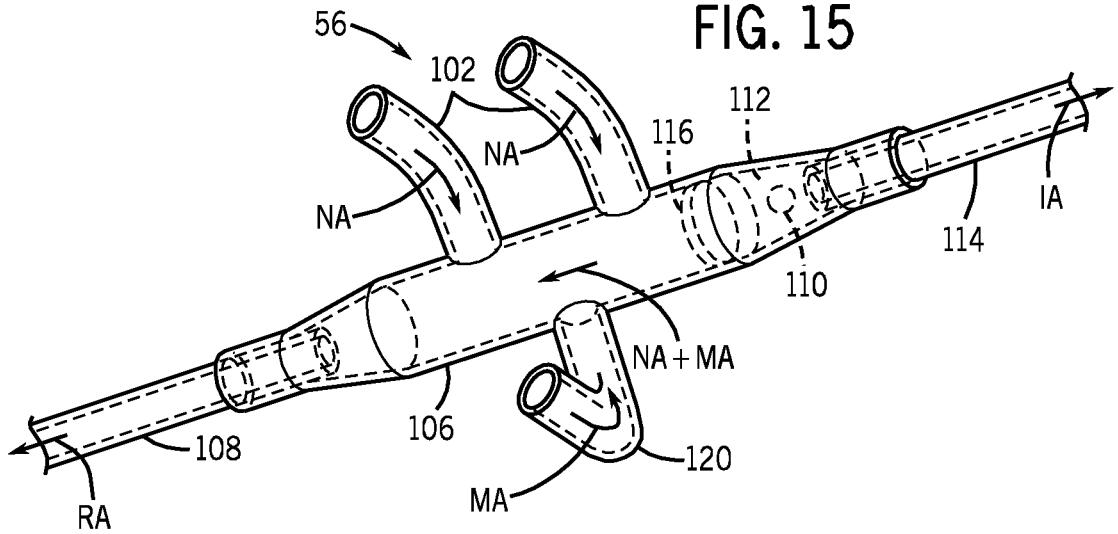
FIG. 15 is a front-perspective view of an oro-nasal cannula receiving the following:
  i) nasal airflows and mouth airflows as respiratory airflows; and
  ii) interface airflows.
Figure 16:
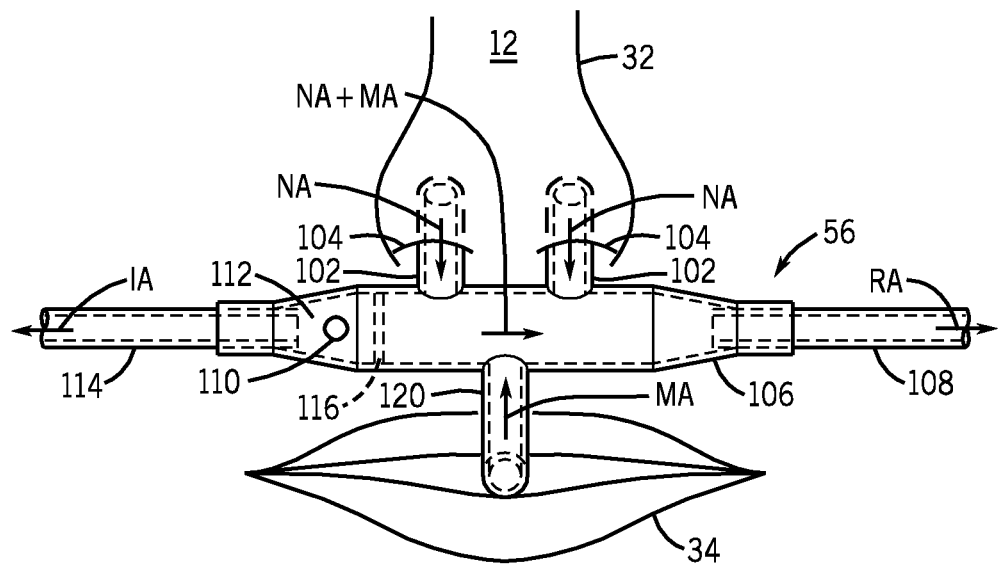
FIG. 16 is a front view of the nasal cannula of FIG. 15.

Referring now to FIGS. 15-16, an oro-nasal cannula 56 is adapted to receive i) nasal airflows NA and mouth airflows MA, and ii) interface airflows IA. More specifically, the oro-nasal cannula 56 includes the one or more nasal prongs 102 and one or more mouth prongs 120 of FIGS. 11-14, particularly for communicating with and/or receiving and/or carrying the nasal airflows NA and mouth airflows MA therefrom. The nasal airflows NA and mouth airflows MA are then communicated by and/or received by and/or carried by the body 106 of the cannula 50 from the nasal prongs 102 and mouth prongs 120 to the respiratory lumen 108. More specifically, the oro-nasal cannula 56 is adapted to receive the nasal airflows NA and mouth airflows MA as respiratory airflows RA for communication to a pneumatic circuit (not shown in FIGS. 15-16) via the respiratory lumen 108, particularly as previously described. This is advantageous, for example, since subjects 12 often alternative between breathing through their nose 32 and mouth 34, particularly if one is or becomes occluded. In this arrangement, respiratory airflows RA can be suitably sampled from either or both of the subject's 12 oro-nasal passages.

In addition, the body 106 of the cannula 50 preferably contains the interface orifice 110 on the external surface 112 thereof, particularly for communicating with and/or receiving and/or carrying the interface airflows IA therefrom, as received by and/or in the area 38 within the interface 26. The interface airflows IA are then communicated by and/or received by and/or carried by the body 106 of the cannula 50 from the interface orifice 110 to the interface lumen 114. More specifically, the cannula 50 is adapted to receive the interface airflows IA for communication to the pneumatic circuit via the interface lumen 114.

Preferably, the respiratory airflows RA and interface airflows IA are received on opposing sides of the dividing partition 116 internally disposed within the body 106 of the cannula 50. Preferably, this partition 116 is configured to divide the body 106 of the cannula 50 into the one or more chambers, at least one of which is configured to receive the respiratory airflows RA and at least one of which is configured to receive the interface airflows IA.

In these FIG. 11-16 embodiments and others, it is generally preferred to locate the interface orifice 110 on an external surface 112 of the cannula 50 that is generally distal or otherwise removed from the subject 12, particularly to avoid any possible interference therewith and allow the interface airflows IA to be received thereby without undue hindrance, as needed and/or desired.

As described in reference to FIGS. 11-16, the respiratory airflows RA and interface airflows IA are preferably received on opposing sides of the dividing partition 116 internally disposed within the body 106 of the cannula 50. Alternatively, this dividing partition 116 can be eliminated by the embodiments shown in FIGS. 17-19.

Figure 17:
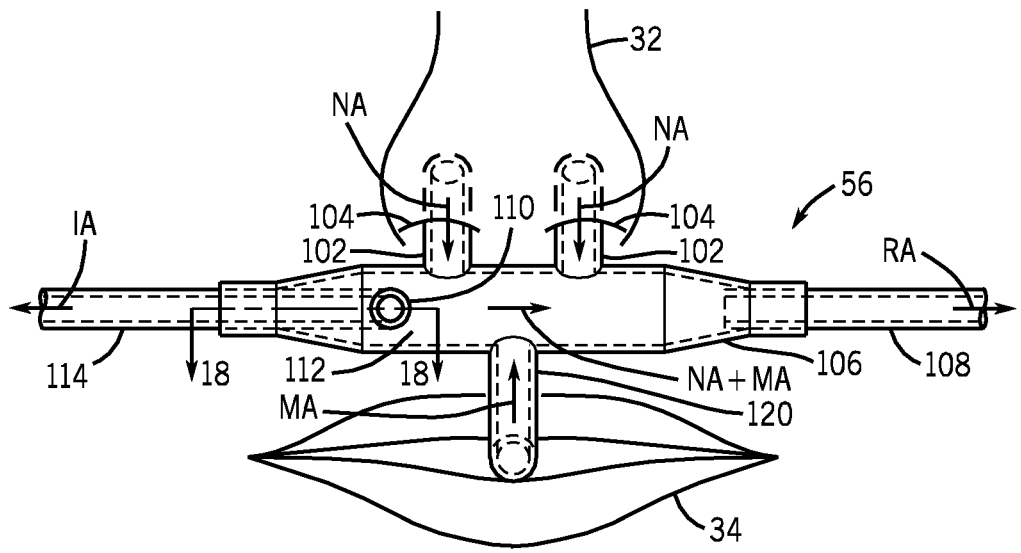
FIG. 17 is a front view of an oro-nasal cannula receiving the following:
  i) nasal airflows and mouth airflows as respiratory airflows; and
  ii) interface airflows in direct connection through the cannula.
Figure 18:
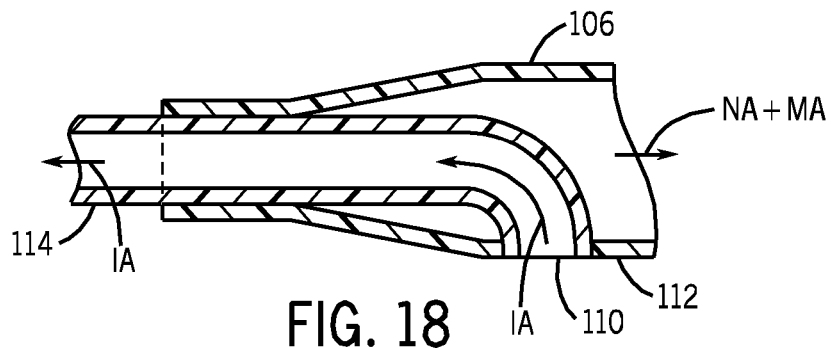
FIG. 18 is a cut-away view taken along line 18-18 in FIG. 17, depicting the direct connection through the cannula in more detail.

More specifically, referring now to FIGS. 17-18, the interface airflows IA are directly received by passing the interface lumen 114 through the body 106 of the cannula 50. More specifically, instead of configuring the partition 116 to divide the body 106 of the cannula 50 into the one or more chambers, that need can be eliminated if the interface airflows IA are directly connected to the interface lumen 114 through the cannula 50. For example, the dividing partition 116 in FIGS. 11-16 separated the respiratory airflows RA and interface airflows IA, particularly so as to not co-mingle. This is similarly accomplished in FIGS. 17-18 by directly connecting the interface lumen 114 to the interface orifice 110 through the body 106 of the cannula 50, without the need to otherwise partition the body 106 of the cannula 50 into the one or more chambers.

Figure 19:
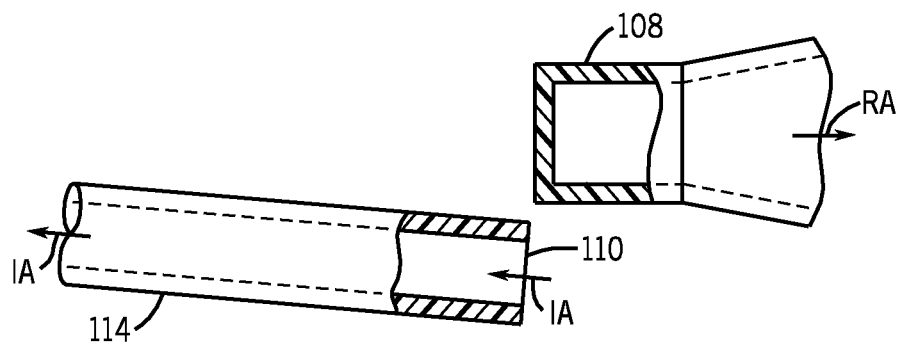
FIG. 19 is a partial view of a cannula receiving interface airflows in open connection with an interface.

Referring now to FIG. 19, the interface airflows IA can also be received in open connection with the area 38 within the interface 26, in which case the interface lumen 114 is in open communication with the area 38 without aid or other support from the body 106 of the cannula 50. More specifically, this embodiment eliminates the need to provide the dividing partition 116 of the cannulas 50 of FIGS. 11-16, as well as the interface orifice 110 on the external surface 112 of the cannula 50. Rather, the interface orifice 110 is thus in open connection with the area 38 within the interface 26 without benefit of the cannulas 50.

Figure 20:
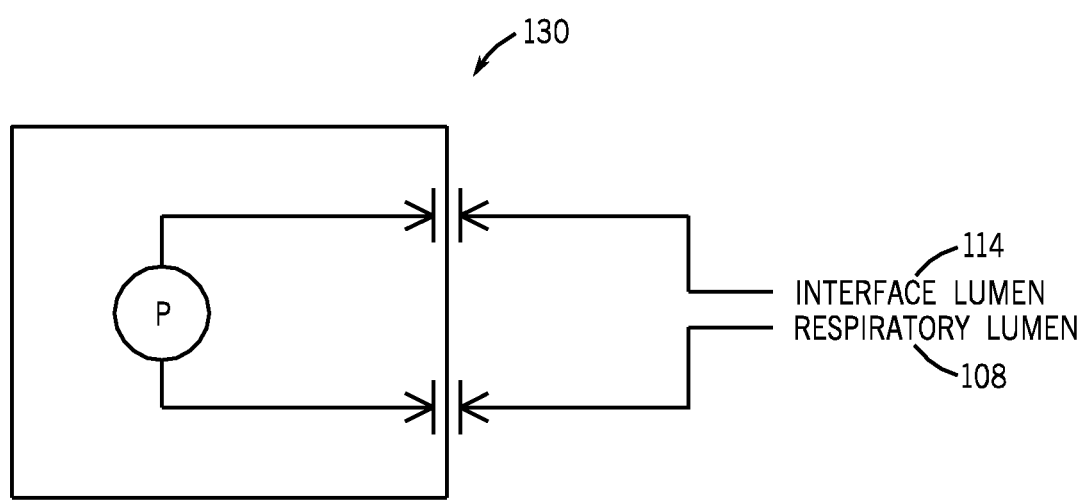
FIG. 20 is a simplified pneumatic circuit for sensing pressure differentials between the following:
  i) respiratory airflows and interface airflows;
  particularly according to a first preferred embodiment, having a single differential pressure transducer.

Referring now to FIG. 20, the respiratory airflows RA are received from the respiratory lumens 108 of the cannulas 50 of FIGS. 11-19, as well as the interface airflows IA from the interface lumens 114, via a pneumatic circuit 130 adapted in communication therewith. More specifically, the pneumatic circuit 130 includes a differential pressure transducer P for comparing pressure differentials between the respiratory airflows RA and interface airflows IA, particularly according to the inventive arrangements, such as described in FIGS. 7-10 and all hereinout, for example. By these arrangements, pressure differentials between the respiratory airflows RA and interface airflows IA can be evaluated without regard to whether the respiratory airflows RA and interface airflows IA are individually increasing or decreasing. Rather, the resulting differential pressures therebetween are determined and/or interpreted for their likely significance as respiratory events and/or non-respiratory events (e.g., likely compressions and/or leaks at the interfaces 26 and/or breathing circuit).

Figure 21:
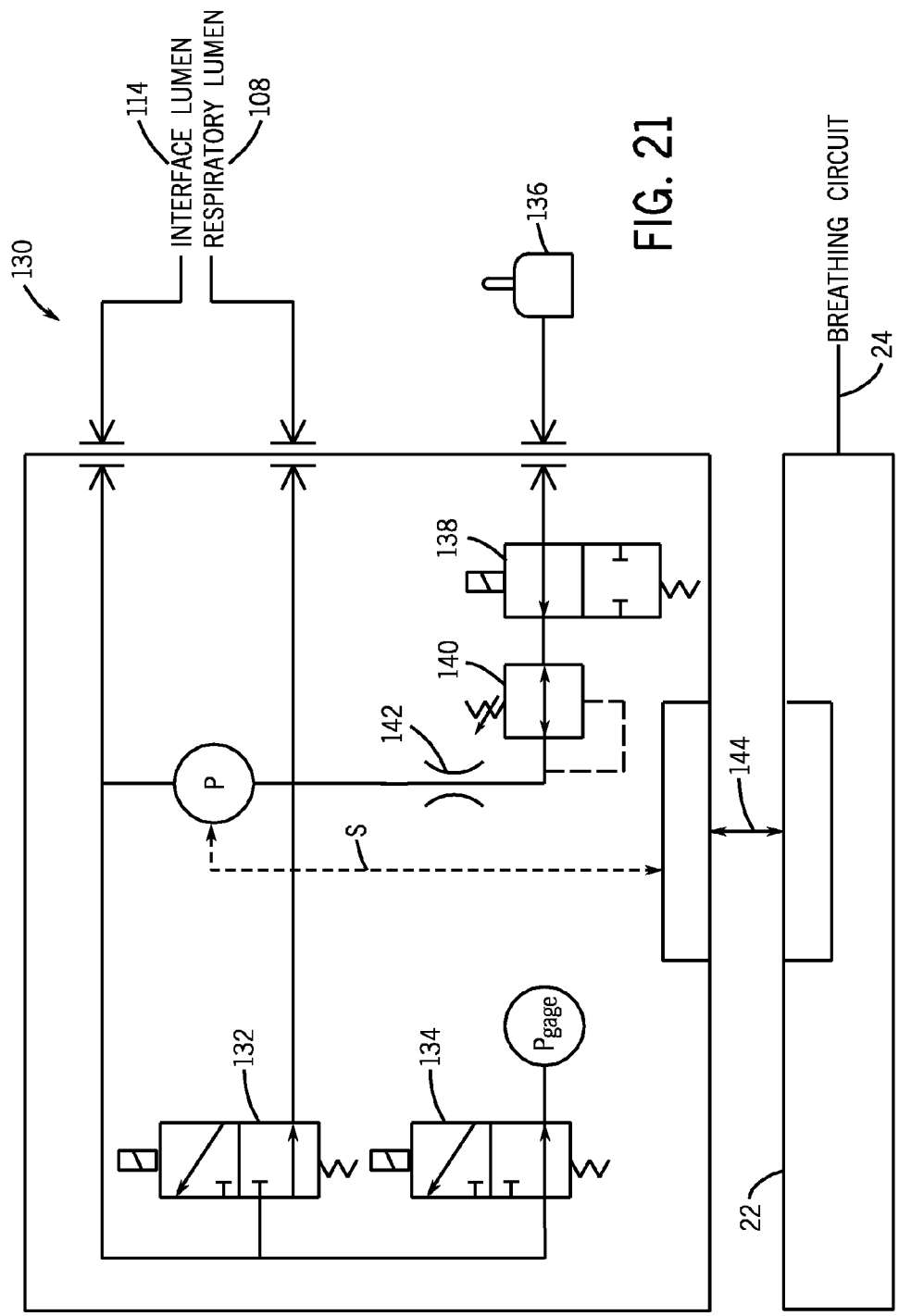
FIG. 21 is an alternative view of the pneumatic circuit of FIG. 20, particularly having calibration valves, $P_{gage}$, and/or ventilator control.

Referring now to FIG. 21, the pneumatic circuit 130 of FIG. 20 can also be expanded to include a pressure transducer $P_{gage}$ in communication with the interface lumen 114 for accurately measuring the pressure at the interface lumen 114 relative to ambient pressure. Alternatively, if the pressure transducer $P_{gage}$ is instead or additionally connected to the respiratory lumen 108, the gage pressure signal can be compared to the ventilator's 22 gage pressure signal to assess whether airflows are entering or exiting the subject 12, thereby serving as a double-check on the differential pressure transducer P.

In addition, a first calibration valve 132 (e.g., a zeroing valve) can be placed in parallel with the differential pressure transducer P for short circuiting the interface lumen 114 and respiratory lumen 108, and a second calibration valve 134 (e.g., another zeroing valve) can be placed in series with the interface lumen 114 and pressure transducer $P_{gage}$ for calibrating the pressure transducer $P_{gage}$. In addition, the respiratory lumen 108 can be cleared of any obstructions therewithin (e.g., mucus, etc.) by providing a purge gas source 136 in communication with the respiratory lumen 108 through a valve 138 (e.g., a 2-way solenoid valve) and/or pressure regulator 140 and/or flow restrictor 142, the latter of which prevents the respiratory lumen 108 from short circuiting with the interface lumen 114 via the purge lines.

These purge components (e.g., purge gas source 136, valve 138, pressure regulator 140, and/or flow restrictor 142) can purge the respiratory lumen 108 either periodically or continuously, as needed and/or desired. In addition, the purge can come from a variety of suitable sources, such as, for example, the purge gas source 136 (e.g., an air source), a plumed wall supply (not shown), a purge-outlet (not shown) on the ventilator 22, and/or the like.

In addition, a power/communication link 144 can also be provided between the pneumatic circuit 130 and ventilator 22, particularly for controlling the latter. For example, an output signal S from the differential pressure transducer P, which can be integrated with, proximal, or distal the cannula 50 to which it is attached and/or in communication with (but not otherwise shown in FIGS. 20-21), can be directed to the ventilator 22, which is configured to respond to the pressure differentials. Accordingly, the differential pressure transducer P is configured to effectuate a change in a breathing circuit of a subject 12 in response to the sensed pressure differentials by the differential pressure transducer P, and improved ventilator control is thereby provided, delivering ventilated support that is synchronized with the subject's 12 own respiratory efforts, leaks and/or compressions notwithstanding.

Figure 22:
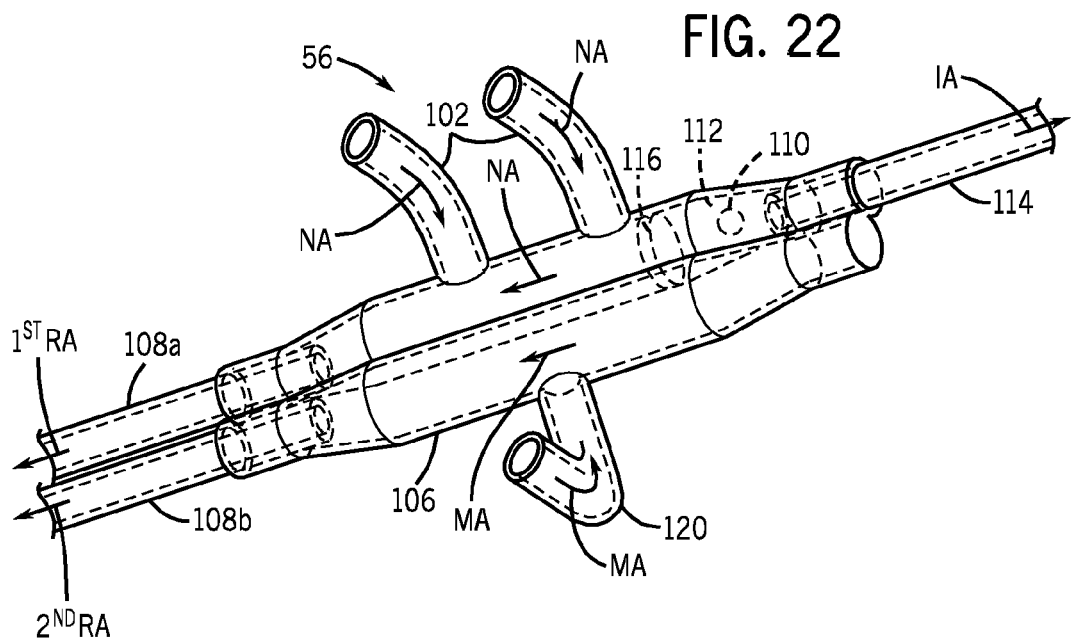
FIG. 22 is a front-perspective view of an oro-nasal cannula receiving the following:
  i) nasal airflows as first respiratory airflows;
  ii) mouth airflows as second respiratory airflows; and
  iii) interface airflows.

Referring now to FIG. 22, the oro-nasal cannula 56 has been re-configured to receive i) nasal airflows NA as first respiratory airflows $1^{st}$ RA, ii) mouth airflows MA as second respiratory airflows $2^{nd}$ RA, and iii) interface airflows IA. More specifically, the oro-nasal cannula 56 includes the one or more nasal prongs 102 and one or more mouth prongs 120 of FIGS. 11-19, particularly for communicating with and/or receiving and/or carrying the nasal airflows NA and mouth airflows MA therefrom. However, the nasal airflows NA are communicated by and/or received by and/or carried by the body 106 of the cannula 50 from the nasal prong 102 to a first respiratory lumen 108a, while the mouth airflows MA are communicated by and/or received by and/or carried by the body 106 of the cannula 50 from the mouth prong 120 to a second respiratory lumen 108b. More specifically, the oro-nasal cannula 56 is adapted to receive the nasal airflows NA as first respiratory airflows $1^{st}$ RA for communication to the pneumatic circuit (not shown in FIG. 22) via the first respiratory lumen 108a, while the oro-nasal cannula 56 is adapted to receive the mouth airflows MA as second respiratory airflows $2^{nd}$ RA for communication to the pneumatic circuit via the second respiratory lumen 108b. Internally within the body 106 of the oro-nasal cannula 56 of FIG. 22, the nasal airflows NA and mouth airflows MA are separable and distinct, whereas in FIGS. 15-18, for example, they can be combined therewithin the body 106 of the cannula 50.

As previously described, the body 106 of the cannula 50 still preferably contains the interface orifice 110 on an external surface 112 thereof, particularly for communicating with and/or receiving and/or carrying the interface airflows IA therefrom, as received by and/or in the area 38 within the interface 26. The interface airflows IA are then communicated by and/or received by and/or carried by the body 106 of the cannula 50 from the interface orifice 110 to the interface lumen 114, as before. More specifically, the cannula 50 is adapted to receive the interface airflows IA for communication to the pneumatic circuit via the interface lumen 114, and they can be received by either or both of the portions of the cannula 50 that receive the nasal airflows NA (as shown in the figure) and/or the mouth airflows (not shown in the figure, but easily understood).

Preferably, the respiratory airflows RA—whether they are the first respiratory airflows $1^{st}$ RA from the nasal airflows NA and/or second respiratory airflows $2^{nd}$ RA from the mouth airflows MA—and interface airflows IA are received on opposing sides of the dividing partition 116 internally disposed within the body 106 of the cannula 50. Preferably, this partition 116 is configured to divide at least a portion of the body 106 of the cannula 50 into the one or more chambers, at least one of which is configured to receive the above-described respiratory airflows RA and at least one of which is configured to receive the above-described interface airflows IA.

Figure 23:
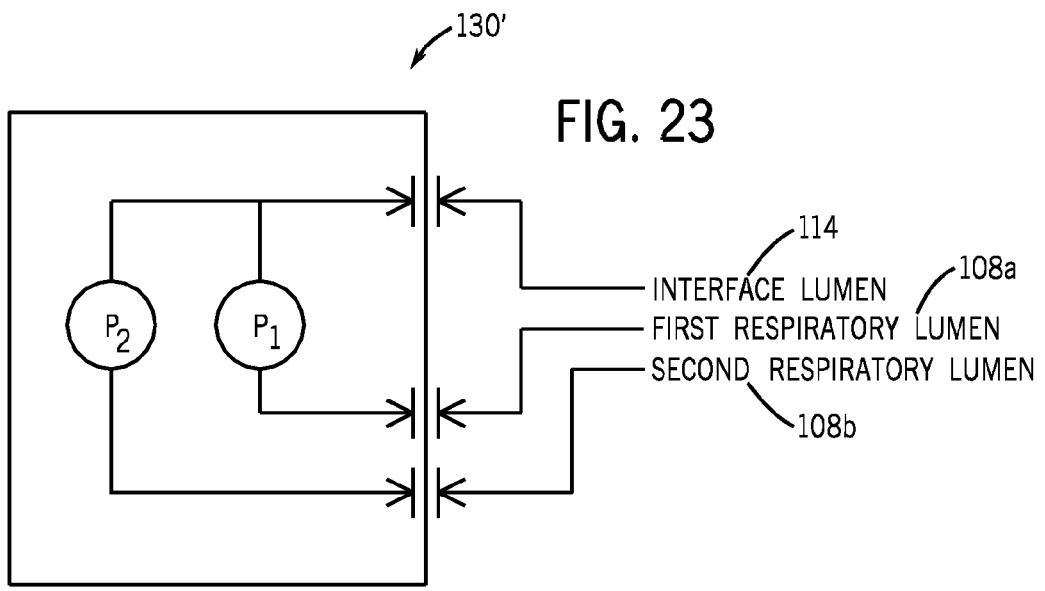
FIG. 23 is a simplified pneumatic circuit for sensing pressure differentials between the following:
  i) first respiratory airflows and interface airflows; and
  ii) second respiratory airflows and interface airflows;
  particularly according to a second preferred embodiment, having multiple differential pressure transducers.

Referring now to FIG. 23, the first respiratory airflows $1^{st}$ RA are received from the first respiratory lumen 108a of the oro-nasal cannula 56 of FIG. 22, as well as the second respiratory airflows $2^{nd}$ RA from the second respiratory lumen 108b, as well as the interface airflows IA from the interface lumens 114, all via the pneumatic circuit 130' adapted in communication therewith. More specifically, the pneumatic circuit 130' now includes a first differential pressure transducer $P_1$ for comparing pressure differentials between the first respiratory airflows $1^{st}$ RA and interface airflows IA, as well as a second differential pressure transducer $P_2$ for comparing pressure differentials between the second respiratory airflows $2^{nd}$ RA and interface airflows IA, particularly according to the inventive arrangements, such as described in FIGS. 7-10 and all hereinout, for example. By these arrangements, pressure differentials between the first respiratory airflows $1^{st}$ RA and interface airflows IA, as well as between the second respiratory airflows $2^{nd}$ RA and interface airflows IA, can be evaluated without regard to whether the first respiratory airflows $1^{st}$ RA and/or second respiratory airflows $2^{nd}$ RA and interface airflows IA are individually increasing or decreasing. Rather, the resulting differential pressures therebetween are determined and/or interpreted for their likely significance as respiratory events and/or non-respiratory events (e.g., likely compressions and/or leaks at the interfaces 26 and/or breathing circuit).

Figure 24:
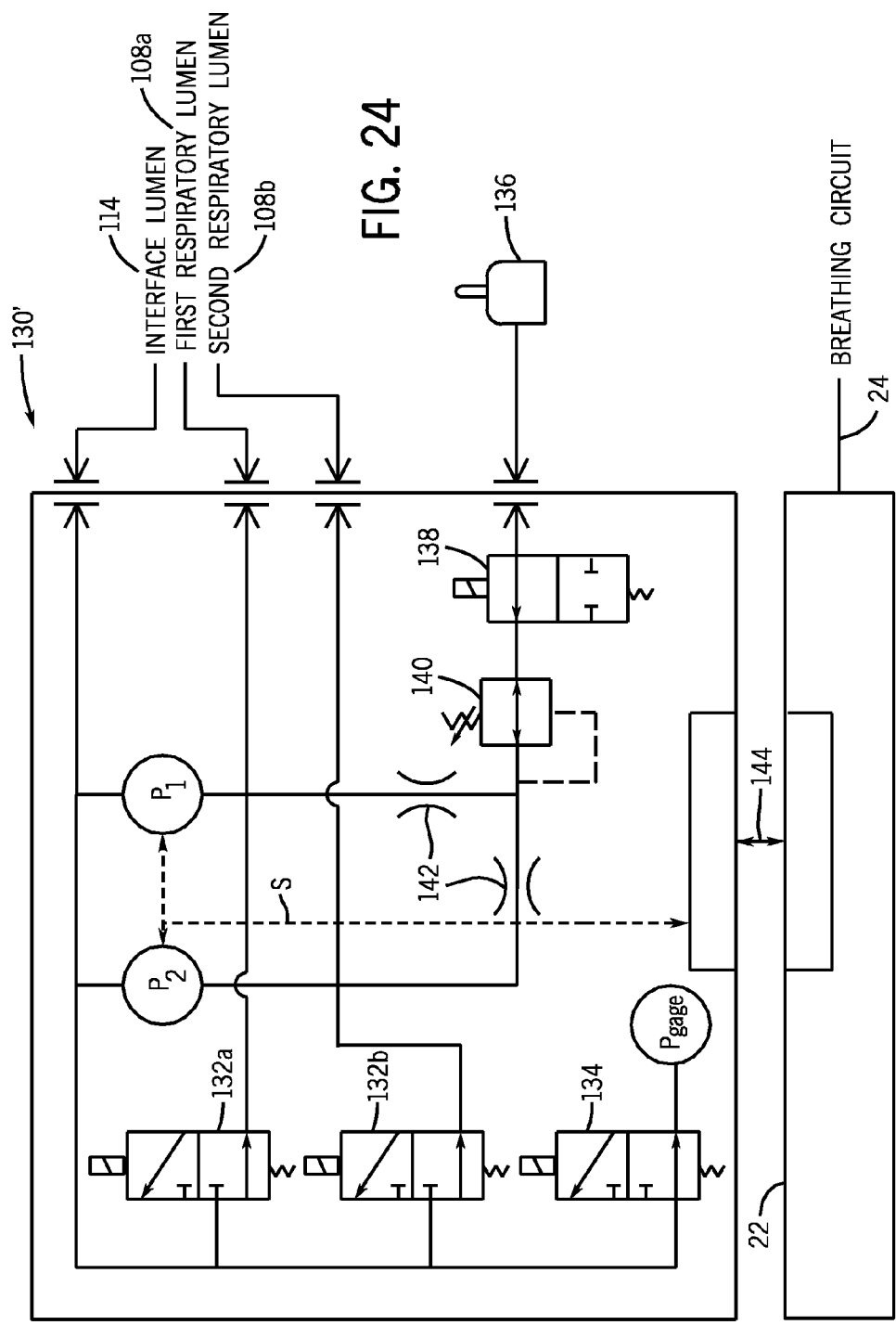
FIG. 24 is an alternative view of the pneumatic circuit of FIG. 23, particularly having calibration valves, $P_{gage}$, and/or ventilator control.

Referring now to FIG. 24, the pneumatic circuit 130' of FIG. 23 can also be expanded to include the pressure transducer $P_{gage}$ in communication with the interface lumen 114 for accurately measuring the pressure at the interface lumen 114 relative to ambient pressure. Alternatively, if the pressure transducer $P_{gage}$ is instead or additionally connected to the first respiratory lumen 108a and/or second respiratory lumen 108b, the gage pressure signal can be compared to the ventilator's 22 gage pressure signal to assess whether airflows are entering or exiting the subject 12, thereby serving as a double-check on the first differential pressure transducer $P_1$ and/or second differential pressure transducer $P_2$.

In addition, a first calibration valve 132a (e.g., a zeroing valve) can be placed in parallel with the first differential pressure transducer $P_1$ for short circuiting the interface lumen 114 and first respiratory lumen 108a, as well as another calibration valve 132b (e.g., another zeroing valve) in parallel with the second differential pressure transducer $P_2$ for short circuiting the interface lumen 114 and second respiratory lumen 108b, and a second calibration valve 134 can be placed in series with the interface lumen 114 and pressure transducer $P_{gage}$ for calibrating the pressure transducer $P_{gage}$. In addition, the first respiratory lumen 108a and/or second respiratory lumen 108b can be cleared of any obstructions therewithin (e.g., mucus, etc.) by providing the purge gas source 136 in communication with the first respiratory lumen 108a and/or second respiratory lumen 108b through a valve 138 (e.g., a 2-way solenoid valve) and/or pressure regulator 140 and/or flow restrictors 142, the latter of which prevents the first respiratory lumen 108a and/or second respiratory lumen 108b from short circuiting with the interface lumen 114 via the purge lines.

These purge components (e.g., purge gas source 136, valve 138, pressure regulator 140, and/or flow restrictor 142) can purge the first respiratory lumen 108a and/or second respiratory lumen 108b either periodically or continuously, as needed and/or desired. In addition, the purge can come from a variety of suitable sources, such as, for example, the purge gas source 136 (e.g., an air source), a plumed wall supply (not shown), a purge outlet (not shown) on the ventilator 22, and/or the like.

In addition, a power/communication link 144 can also be provided between the pneumatic circuit 130' and ventilator 22, particularly for controlling the latter. For example, an output signal S from the first differential pressure transducer $P_1$ and/or second differential pressure transducer $P_2$, which can be integrated with, proximal, or distal the cannula 50 to which they are attached and/or in communication therewith (but not otherwise shown in FIGS. 23-24), can be directed to the ventilator 22, which is configured to respond to the pressure differentials. Accordingly, the first differential pressure transducer $P_1$ and/or second differential pressure transducer $P_2$ are configured to effectuate a change in a breathing circuit of the subject in response to the sensed pressure differentials by the first differential pressure transducer $P_1$ and/or second differential pressure transducer $P_2$, and improved ventilator control is thereby provided, delivering ventilated support that is synchronized with the subject's 12 own respiratory efforts, leaks and/or compressions notwithstanding.

In addition, the inventive arrangements can be arranged to monitor exhaled gases, such as carbon dioxide $CO_2$, in addition to the respiratory airflows RA and interface airflows IA.

Figure 25:
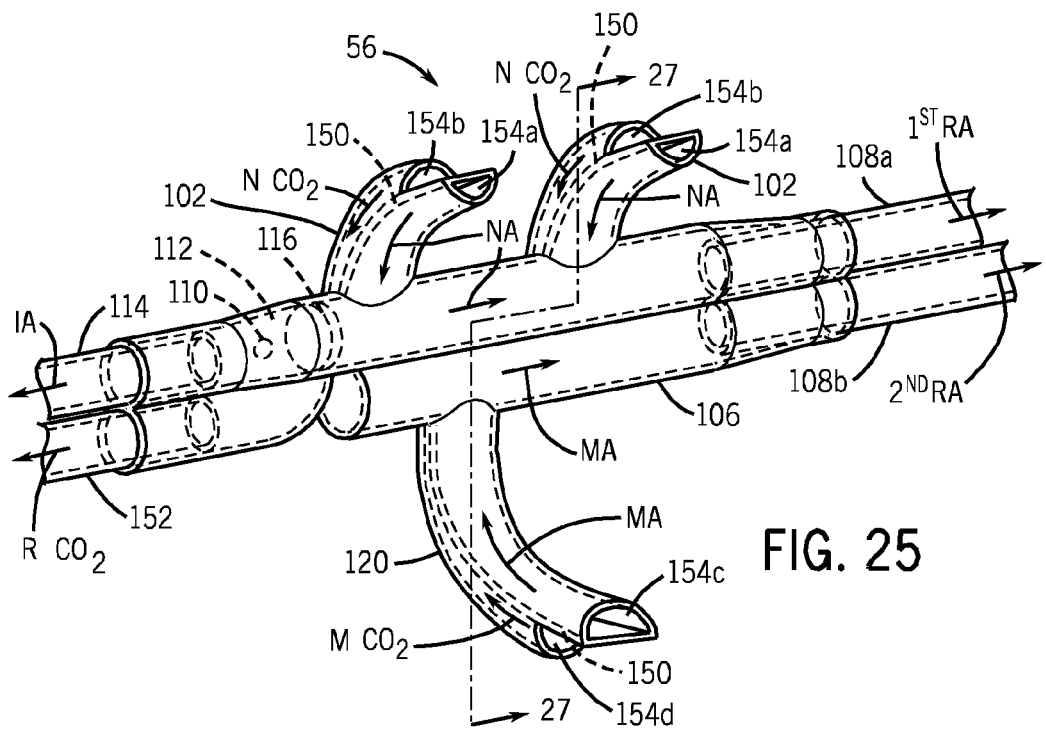
FIG. 25 is a front-perspective view of an oro-nasal cannula receiving the following:
  i) nasal airflows as first respiratory airflows;
  ii) mouth airflows as second respiratory airflows;
  iii) nasal $CO_2$ and mouth $CO_2$ as respiratory $CO_2$; and
  iv) interface airflows;
  particularly according to a first preferred embodiment, having bifurcated prong capture.
Figure 26:
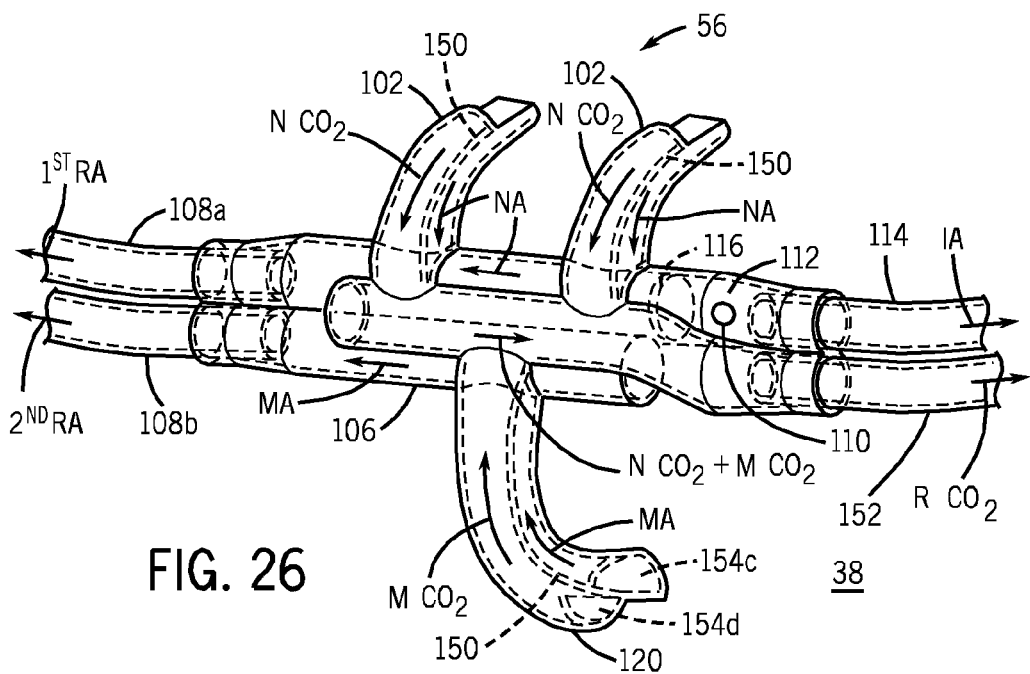
FIG. 26 is a rear-perspective view of the oro-nasal cannula of FIG. 25.
Figure 27:
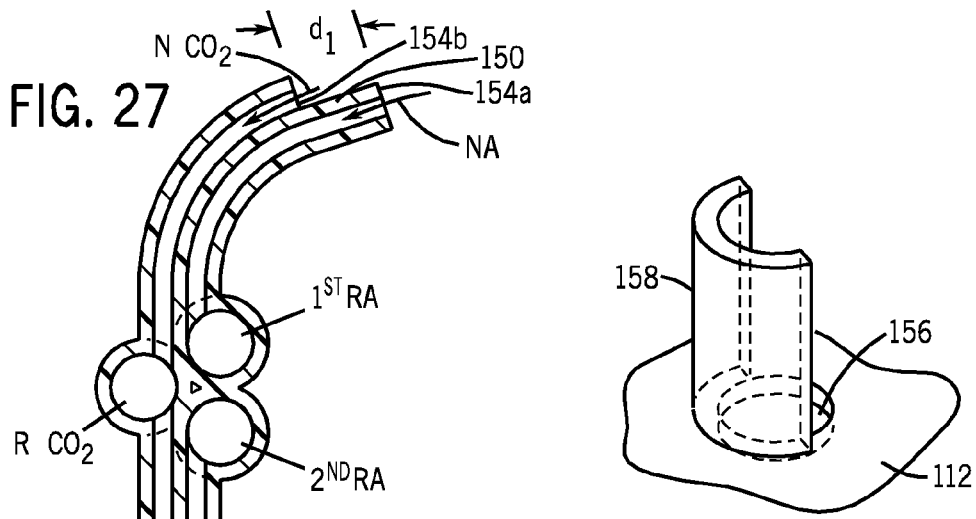
FIG. 27 is a cut-away view taken along line 27-27 of FIG. 25.

Referring now to FIGS. 25-27, for example, the nasal prongs 102 and/or mouth prongs 120 can be bifurcated to receive both i) nasal airflows NA and/or mouth airflows MA, as well as ii) nasal carbon dioxide N $CO_2$ and/or mouth carbon dioxide M $CO_2$. More specifically, either or both of the nasal prongs NA and/or mouth prongs MA contain an internal dividing wall 150 therewithin to separate collection of i) the nasal airflows NA and/or mouth airflows MA from ii) the nasal carbon dioxide N $CO_2$ and/or mouth carbon dioxide M $CO_2$. The nasal carbon dioxide N $CO_2$ and/or mouth carbon dioxide M $CO_2$ are representative of exhaled gases that can be sampled by the oro-nasal cannula 56 in FIGS. 25-34, with other exhaled gases and/or other cannulas 50 being likewise suitably arranged (but not otherwise shown in FIGS. 25-27).

More specifically, the oro-nasal cannula 56 includes the familiar one or more nasal prongs 102 and one or more mouth prongs 120 of FIGS. 11-19, particularly for communicating with and/or receiving and/or carrying the nasal airflows NA and mouth airflows MA therefrom. However, the one or more nasal prongs 102 and one or more mouth prongs 120 are also now configured to communicate with and/or receive and/or carry the nasal carbon dioxide N $CO_2$ and/or mouth carbon dioxide M $CO_2$ therefrom as well.

As per the particular oro-nasal cannula 56 of FIG. 22, it has been re-configured to receive i) nasal airflows NA as first respiratory airflows $1^{st}$ RA, ii) mouth airflows MA as second respiratory airflows $2^{nd}$ RA, iii) interface airflows IA, and iv) respiratory carbon dioxide R $CO_2$. As previously described, the nasal airflows NA are again communicated by and/or received by and/or carried by the body 106 of the cannula 50 from the nasal prong 102 to the first respiratory lumen 108a, while the mouth airflows MA are again communicated by and/or received by and/or carried by the body 106 of the cannula 50 from the mouth prong 120 to the second respiratory lumen 108b. As previously described, the oro-nasal cannula 56 is again adapted to receive the nasal airflows NA as first respiratory airflows $1^{st}$ RA for communication to the pneumatic circuit (not shown in FIGS. 25-27) via the first respiratory lumen 108a, as well as again adapted to receive the mouth airflows MA as second respiratory airflows $2^{nd}$ RA for communication to the pneumatic circuit 130' via the second respiratory lumen 108b.

As previously described, the body 106 of the cannula 50 still preferably contains the interface orifice 110 on an external surface 112 thereof, particularly for communicating with and/or receiving and/or carrying the interface airflows IA therefrom, as received by and/or in the area 38 within the interface 26. Again, the interface airflows IA are then communicated by and/or received by and/or carried by the body 106 of the cannula 50 from the interface orifice 110 to the interface lumen 114, as before, as well as including arrangements such as i) the dividing partition 116 internally disposed within the body 106 of the cannula 50 to divide the same into the one or more chambers, at least one of which is configured to receive the respiratory airflows RA and at least one of which is configured to receive the interface airflows IA, ii) the direct connection (e.g., see FIG. 18), or iii) the open connection (e.g., see FIG. 19)—all as previously described.

Now then, while the nasal airflows NA and mouth airflows MA continue to be communicated by and/or received by and/or carried by the body 106 of the cannula 50 from the nasal prongs 102 and/or mouth prongs 120 to the first respiratory lumen 108a and/or second respiratory lumen 108b, the nasal carbon dioxide N $CO_2$ and/or mouth carbon dioxide M $CO_2$ are also communicated by and/or received by and/or carried by the body 106 of the cannula 50 from the nasal prongs 102 and/or mouth prongs 120 to a respiratory carbon dioxide lumen 152. More specifically, the oro-nasal cannula 56 is now adapted to receive the nasal carbon dioxide N $CO_2$ and/or mouth carbon dioxide M $CO_2$ as the respiratory carbon dioxide R $CO_2$ for communication to a pneumatic circuit (not shown in FIGS. 25-27) via the respiratory carbon dioxide lumen 152.

As described, the nasal prong 102 and/or mouth prong 120 preferably contain the internal dividing wall 150 therewithin to separate i) the nasal airflows NA from the nasal carbon dioxide N $CO_2$, and/or ii) the mouth airflows MA from the mouth carbon dioxide M $CO_2$, each preferably having its own receiving orifice 154 at a distal end of the appropriate prong 102, 120.

Preferably, the exhaled gas sampling portion of the prong 102, 120 is set back from the respiratory sampling portion of the prong by a suitable distance d, as shown in FIG. 27. Preferably, this setback is chosen to minimize the interference therebetween, particularly enabling accurate sampling of the exhaled gases. In other words, for example, the particular receiving orifice 154a for the nasal airflows NA is preferably non co-planar with the particular receiving orifice 154b for the nasal carbon dioxide N $CO_2$, as represented by the suitable distance $d_1$. In like fashion, for example, the particular receiving orifice 154c for the mouth airflows MA is preferably non co-planar with the particular receiving orifice 154d for the mouth carbon dioxide M $CO_2$, as again represented by the suitable distance $d_2$. These suitable distances $d_1$, $d_2$ may be the same or different, with i) $d_1=d_2$ (i.e., as shown), or ii) $d_1>d_2$, or iii) $d_1<d_2$, or iv) $d_1=0$, and/or v) $d_2=0$, as needed and/or desired.

If the afore-described setback is carried along the entire length of the prong 102, 120, an arrangement such as that depicted in FIGS. 28-31 can be achieved, in which the exhaled gas sampling portion of the nasal prong 102, for example, can instead be carried on the external surface 112 of the body 106 of the cannula 50, suitably now arranged as one or more exhaled gas orifices 156 for receiving the same. This alternatively eliminates the need to bifurcate the prongs 102, 120, in which the applicable receiving orifices 154b, 154d for the exhaled gases on the prongs 102, 120 can be suitably replaced by the exhaled gas orifices 156 carried on the external surface 112 of the body 106 of the cannula 50.

Also in FIGS. 28-31, for example, the bifurcated mouth prong 120 of FIGS. 25-27, for example, can be replaced by multiple mouth prongs 120a, 120b, at least one mouth prong 120a of which is configured to receive the mouth airflows MA and another of which mouth prong 120b is configured to receive the mouth carbon dioxide M $CO_2$. Although not necessarily shown in the figures, the multiple prongs 120a, 120b can again be offset by suitable distance d, as representatively shown more specifically in FIG. 27 (but equally as applicable here), again as needed and/or desired.

While several of the above-described modifications to FIGS. 25-27 were reflected in FIGS. 28-31 as applying to one or the other of the nasal prong 102 and/or mouth prong 120, these modifications were only representatively depicted. For example, while the bifurcated nasal prong 102 was altered to include the exhaled gas orifices 156, the bifurcated mouth prong 120 can also be similarly altered. Likewise, while the bifurcated mouth prong 120 was altered to include the multiple mouth prongs 120a, 120b, the bifurcated nasal prong 120 can also be similarly altered. Accordingly, any or all of these changes may be made separately and/or together, as needed and/or desired.

As previously described in FIGS. 28-31, the exhaled gas sampling portion of the nasal prong 102, for example, can be carried on the external surface 112 of the body 106 of the cannula 50, suitably arranged as one or more exhaled gas orifices 156 for receiving the same. This arrangement can be further enhanced by a configuration shown in FIGS. 32-33, for example, in which the exhaled gas capture by the exhaled gas orifices 156 is assisted by a capture enhancer 158, such as shield or wall or block or the like, operative in communication therewith. More specifically, the capture enhancer 158 is preferably affixed to the external surface 112 of the cannula 50 by a rib 160 and/or the like, and suitably shaped and sized to channel or otherwise capture the exhaled gases into the exhaled gas orifices 156. It can take numerous alternative forms as well, such as a scooped prong 162, for example, to receive the mouth carbon dioxide M $CO_2$ as well, again suitably shaped and sized to channel or otherwise capture the exhaled gases.

Figure 33:
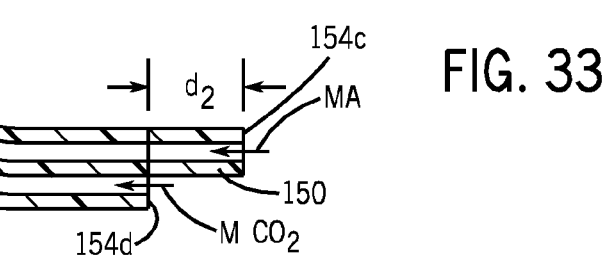
FIG. 33 is a perspective view of an alternative capture enhancer of FIG. 32.
Figure 32:
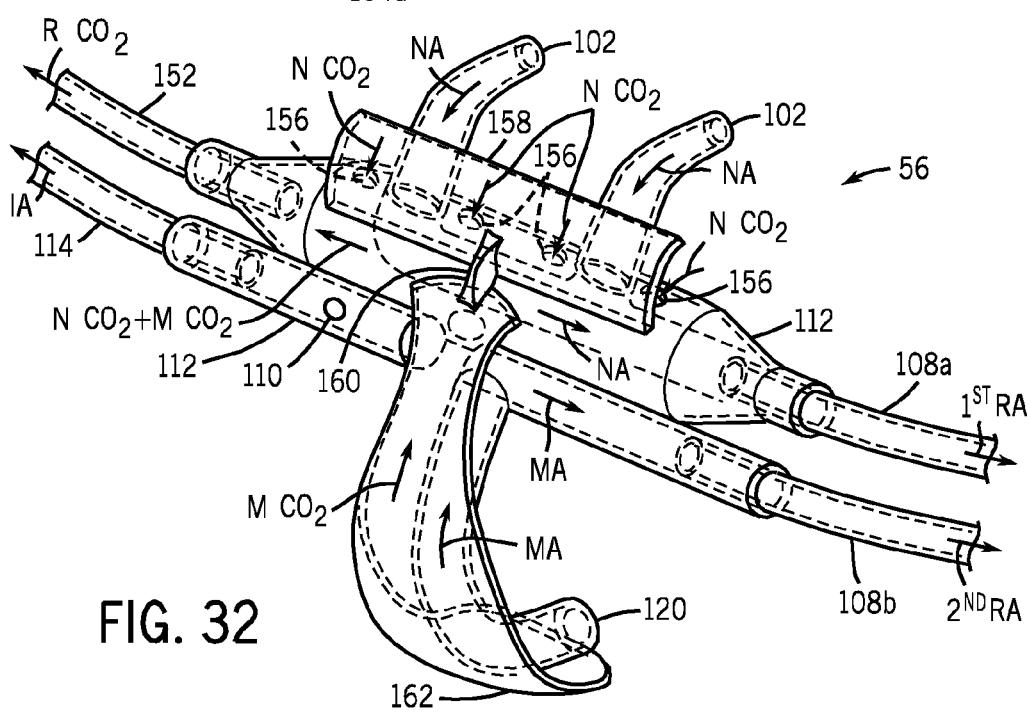
FIG. 32 is a rear-perspective view of an oro-nasal cannula receiving:
  i) nasal airflows as first respiratory airflows;
  ii) mouth airflows as second respiratory airflows;
  iii) nasal $CO_2$ and mouth $CO_2$ as respiratory $CO_2$; and
  iv) interface airflows;
  particularly according to a third preferred embodiment, having a capture enhancer and/or scooped prong capture.
Figure 28:
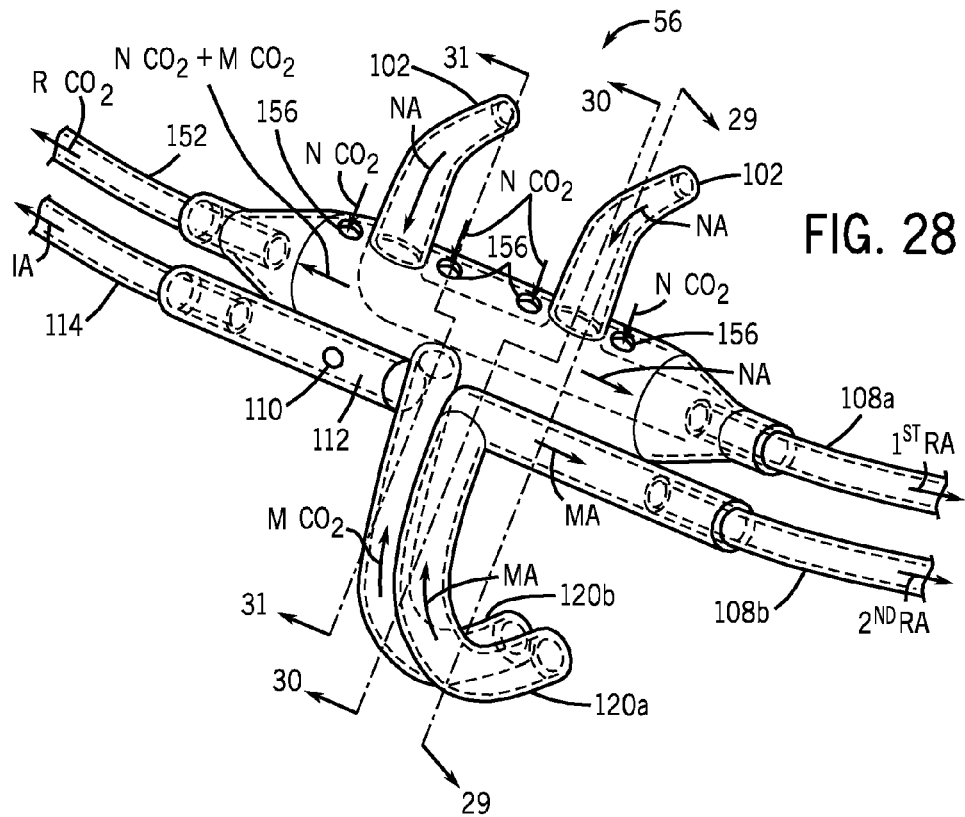
FIG. 28 is a front-perspective view of an oro-nasal cannula receiving the following:
  i) nasal airflows as first respiratory airflows;
  ii) mouth airflows as second respiratory airflows;
  iii) nasal $CO_2$ and mouth $CO_2$ as respiratory $CO_2$; and
  iv) interface airflows;
  particularly according to a second preferred embodiment, having direct and/or offset prong capture.
Figure 29:
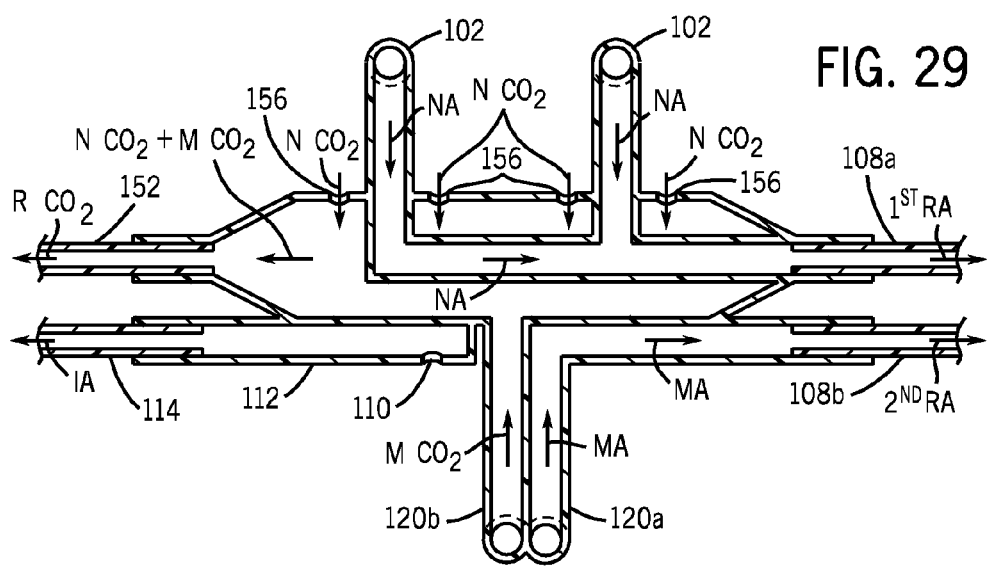
FIG. 29 is a first cut-away view taken along line 29-29 in FIG. 28.

While several of the above-described modification to FIGS. 28-31 were reflected in FIGS. 32-33 as applying to one or the other of the nasal prong 102 or mouth prong 120, these modifications were only representatively depicted. For example, while the capture enhancer 158, such as the shield or wall or block or the like, was applied towards the nasal prongs 102 to assist the nasal carbon dioxide N $CO_2$ capture, it can be readily applied to the mouth prongs 120 as well to assist the mouth carbon dioxide M $CO_2$ capture. Likewise, while the scooped prong 162 was applied towards the mouth prongs 120 to assist the mouth carbon dioxide M $CO_2$ capture, it can be readily applied to the nasal prongs 102 as well to assist the nasal carbon dioxide N $CO_2$ capture. Accordingly, any or all of these changes may be made separately and/or together, as needed and/or desired.

Figure 34:
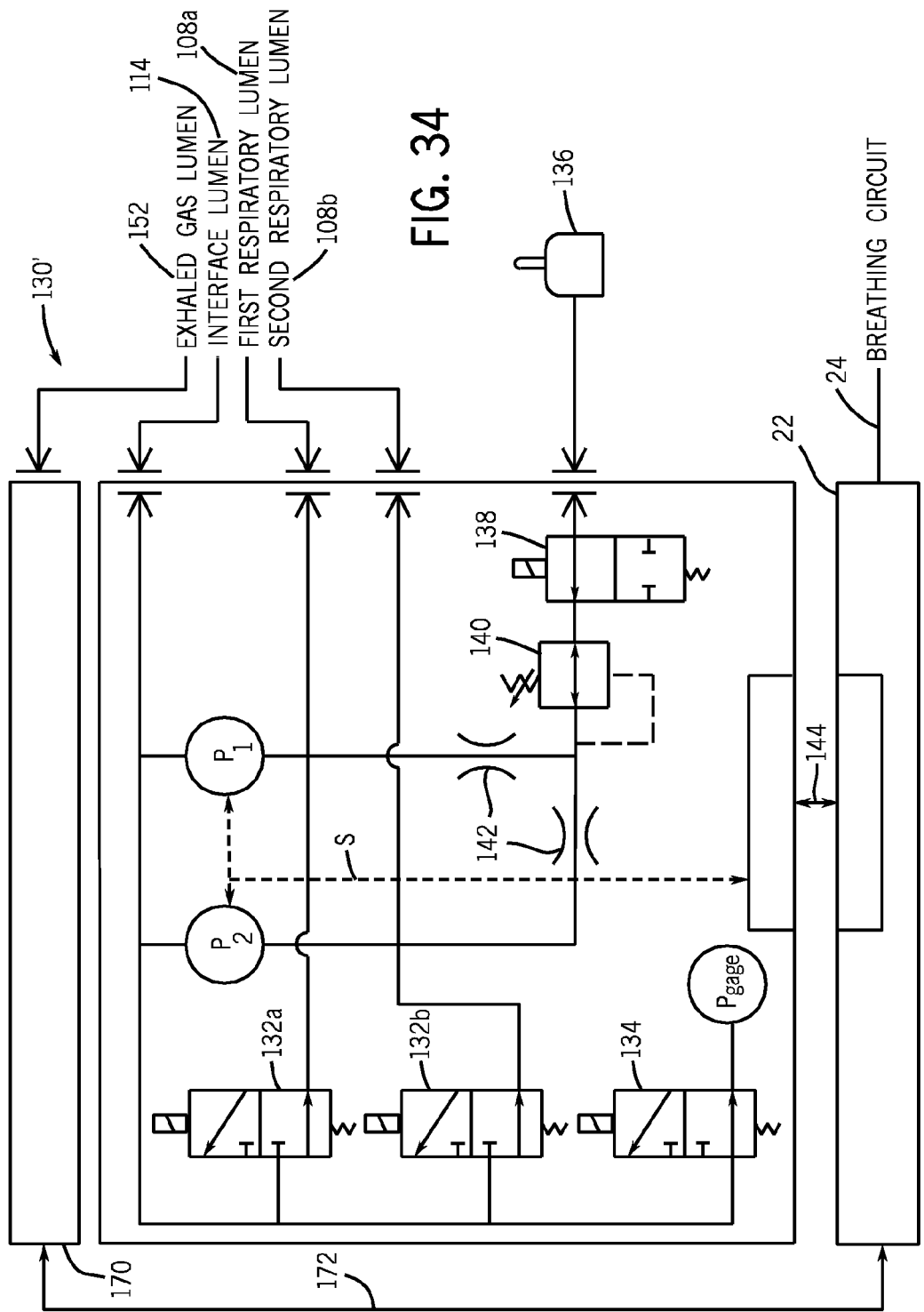
FIG. 34 is a pneumatic circuit for sensing pressure differentials between the following:
  i) first respiratory airflows and interface airflows; and
  ii) second respiratory airflows and interface airflows;
  particularly according to the second preferred embodiment of FIGS. 23-24, having the multiple differential pressure transducers, as well as exhaled gas sampling, calibration valves, $P_{gage}$, and/or ventilator control.

Referring now to FIG. 34, the captured exhaled gases can be routed to a gas analyzer 170. More specifically, in any or all of the FIG. 25-33 embodiments, the exhaled gases can be analyzed in the area 38 within the interface 26, particularly as needed and/or desired. Accordingly, the exhaled gases may be drawn out of the cannulas 50 using suction or a pump (not shown). In any event, the pneumatic circuit 130' of FIG. 24 can now be expanded to include the afore-mentioned gas analyzer 170, configured to receive the exhaled gases from the respiratory carbon dioxide lumen 152.

In addition, a power/communication link 172 can also be provided between the gas analyzer 170 and ventilator 22, particularly for controlling the latter. Accordingly, the pneumatic circuit 130' is now configured to effectuate a change in a breathing circuit of a subject 12 in response to the sensed pressure differentials by the first differential pressure transducer $P_1$ and/or second differential pressure transducer $P_2$ and the exhaled gases by the gas analyzer 170, and improved ventilator control is thereby provided, delivering ventilated support that is synchronized with the subject's 12 own respiratory efforts, leaks and/or compressions notwithstanding, with the remainder of the pneumatic circuit 130' corresponding to FIG. 24, now with even more enhanced ventilator control.

And referring finally to FIG. 35, many of the above-described features are presented in various combinations as a further convenience to the reader in a table 180.

Accordingly, it should be readily apparent that this specification describes illustrative, exemplary, representative, and non-limiting embodiments of the inventive arrangements. Accordingly, the scope of the inventive arrangements are not limited to any of these embodiments. Rather, various details and features of the embodiments were disclosed as required. Thus, many changes and modifications—as readily apparent to those skilled in these arts—are within the scope of the inventive arrangements without departing from the spirit hereof, and the inventive arrangements are inclusive thereof. Accordingly, to apprise the public of the scope and spirit of the inventive arrangements, the following claims are made:

What is claimed is:

1. A respiratory monitoring apparatus for use with a patient, comprising:
   a respiratory lumen coupled to a cannula in use by the patient, wherein the respiratory lumen receives a respiratory airflow from the patient or to the patient;
   an interface lumen having an inlet end positioned in an area near the cannula, wherein the interface lumen receives an interface airflow from the area near the cannula directed either from the patient or to the patient, and
   a differential pressure transducer coupled to both the respiratory lumen and the interface lumen to detect pressure differentials between the respiratory airflow and the interface airflow.

2. The apparatus of claim 1, wherein said area is sealed from airflows external from said area.

3. The apparatus of claim 2, wherein said area comprises a mask, hood, or helmet.

4. The apparatus of claim 1, wherein said differential pressure transducer is configured to receive said respiratory airflows from a nose of said subject.

5. The apparatus of claim 1, wherein said differential pressure transducer is configured to receive said respiratory airflows from a mouth of said subject.

6. The apparatus of claim 1, wherein said differential pressure transducer is configured to receive said respiratory airflows from is nose of said subject and a mouth of said subject.

7. The apparatus of claim 1, wherein said differential pressure transducer is configured to receive said interface airflows in direct connection through said cannula.

8. The apparatus of claim 1, wherein said differential pressure transducer is configured to receive said interface airflows in open connection with said area.

9. The apparatus of claim 1 further comprising a ventilator in communication with the differential pressure transducer, wherein the ventilator identifies a respiratory event or a non-respiratory event based on the pressure differentials from the differential pressure transducer.

10. The apparatus of claim 9, wherein said ventilator is configured to respond to said pressure differentials.

11. The apparatus of claim 9, wherein said ventilator is configured to effectuate a change in a breathing circuit of said subject in response to said pressure differentials.

12. The apparatus of claim 9 wherein the ventilator is coupled to the respiratory lumen and the interface lumen, wherein the ventilator identifies a non-respiratory event if the pressure differentials between the respiratory airflow and the interface airflow remain unchanged.

13. A method of respiratory monitoring, comprising:
   positioning a cannula on the patient, the cannula including a respiratory lumen that receives a respiratory airflow from the patient or to the patient and an interface lumen that receives an interface airflow from an area near the cannula;
   coupling the respiratory lumen and the interface lumen to a differential pressure transducer which is coupled to a ventilator;
   determining a pressure differential with the differential pressure transducer between the respiratory airflow and the interface airflow; and
   identifying a respiratory event or a non-respiratory event in the ventilator based upon the pressure differentials from the differential pressure transducer.

14. The method of claim 13, wherein said cannula is configured to receive said respiratory airflows from a nose of said subject.

15. The method of claim 13, wherein said cannula is configured to receive said respiratory airflows from a mouth of said subject.

16. The method of claim 13, wherein said cannula is configure to receive said respiratory airflows from a nose of said subject and a mouth of said subject.

17. The method of claim 13, wherein said cannula is configured to receive said interface airflows.

18. The method of claim 17, wherein said cannula is configured to receive said interface airflows in direct connection through said cannula.

19. The method of claim 13, wherein said ventilator is configured to respond to said pressure differentials.

20. The method of claim 13 wherein the ventilator determines a respiratory event or a non-respiratory event based upon the respiratory airflow and the interface airflow.

* * * * *